US005580979A

United States Patent [19]
Bachovchin

[11] Patent Number: 5,580,979
[45] Date of Patent: Dec. 3, 1996

[54] PHOSPHOTYROSINE PEPTIDOMIMETICS FOR INHIBITING SH2 DOMAIN INTERACTIONS

[75] Inventor: William W. Bachovchin, Melrose, Mass.

[73] Assignee: Trustees of Tufts University, Medford, Mass.

[21] Appl. No.: 214,643

[22] Filed: Mar. 15, 1994

[51] Int. Cl.$^6$ ................ C07D 243/16; C07D 243/20; C07D 243/22

[52] U.S. Cl. ............... 540/509; 540/505; 540/510; 540/511; 540/542; 540/569; 540/570; 540/571; 540/572

[58] Field of Search .................. 540/509, 510, 540/505, 511, 542, 569, 570, 571, 572

[56] References Cited

U.S. PATENT DOCUMENTS

| | | | |
|---|---|---|---|
| 4,424,226 | 1/1984 | Eberlein et al. | 424/263 |
| 4,594,191 | 6/1986 | Bock et al. | 260/239.3 |
| 4,628,084 | 12/1986 | Bock et al. | 540/509 |
| 4,650,797 | 3/1987 | Atwal | 514/221 |
| 4,755,508 | 7/1988 | Bock et al. | 514/221 |
| 4,820,834 | 4/1989 | Evans et al. | 540/504 |
| 4,898,861 | 2/1990 | Morgan et al. | 514/221 |
| 4,957,915 | 9/1990 | Kim et al. | 514/221 |
| 5,116,971 | 5/1992 | Harreus et al. | 540/362 |
| 5,175,159 | 12/1992 | Bock et al. | 540/309 |

FOREIGN PATENT DOCUMENTS

| | | | |
|---|---|---|---|
| 0490590 | 6/1992 | European Pat. Off. | 540/309 |
| WO92/09297 | 6/1992 | WIPO . | |

OTHER PUBLICATIONS

Science, vol. 260, 1937–1942, 1993.
James, G. L., et al., (1993), "Benzodiazepine Peptoidomimetics: Potent Inhibitors of Ras Farnesylation in Animal Cells", *Science*, vol. 260, pp. 1937–1942.
Eck, M. J., et al., (1993), "Recognition of a high–affinity phosphotyrosyl peptide by the Src homology–2 domain of p56$^{lck}$", *Nature*, vol. 362, pp. 87–91.
Waksman, G., et al., (1993), "Binding of a High Affinity Phosphotyrosyl Peptide to the Src SH2 Domain: Crystal Structures of the Complexed and Peptide–free Forms", *Cell*, vol. 72, pp. 779–790.
Songyang, Z., et al., (1993), "SH2 Domains Recognize Specific Phosphopeptide Sequences", *Cell*, vol. 72, pp. 767–778.
Sierke, S. L., and Koland, J. G., (1993), "SH2 Domain Proteins as High–Affinity Receptor Tyrosine Kinase Substrates", *Biochemistry*, vol. 32, pp. 10102–10108.
Pawson, T. and Gish, G. D., (1992), "SH2 and SH3 Domains: From Structure fo Function", *Cell*, vol. 71, pp. 359–362.
Birge, R. B., et al., (1992), "Tyrosine–phosphorylated Epidermal Growth Factor Receptor and Cellular p130 Provide High Affinity Binding Substrates to Analyze Crk–Phosphotyrosine–dependent Interactions in Virto", *The Journal of Biological Chemistry*, vol. 267, No. 16, pp. 10588–10595.

Petsko, G. A., (1992), "Fishing in Src–infested waters", *Nature*, vol. 358, pp. 625–626.
Fanti, W. J., et al., (1992), "Distinct Phosphotyrosines on a Growth Factor Receptor Bind to Specific Molecules That Mediate Different Signaling Pathways", *Cell*, vol. 69, pp. 413–423.
Domchek, S. M., et al., (1992), "Inhibition of SH2 Domain/Phosphoprotein Association by a Nonhydrolyzable Phosphonopeptide", *Biochemistry*, vol. 31, pp. 9865–9870.
Pendergast, A. M., et al., (1993), "BCR–ABL–Induced Oncogenesis is Mediated by Direct Interaction with the SH2 Domain of the GRB–2 Adaptor Protein", *Cell*, vol. 75, pp. 175–185.

(List continued on next page.)

*Primary Examiner*—Yogendra N. Gupta
*Attorney, Agent, or Firm*—Matthew P. Vincent; Giulio A. DeConti, Jr.; Iahive & Cockfield

[57] ABSTRACT

The present invention makes available novel compounds represented by the general formula

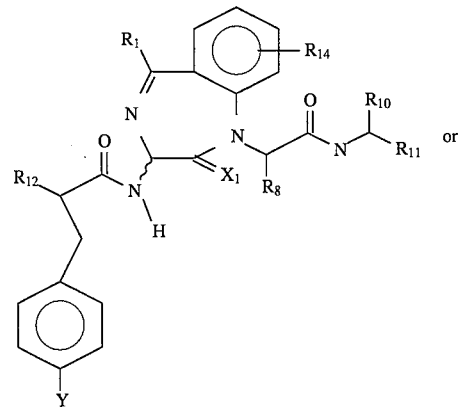

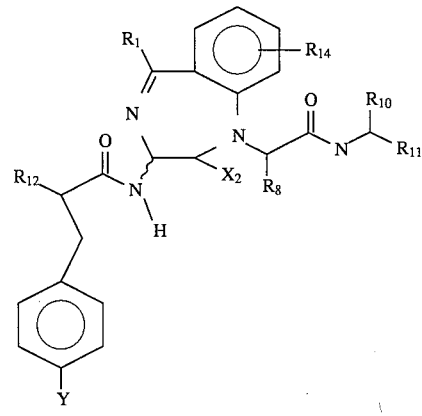

wherein Y represents a phosphate analog. Which compounds are useful for inhibiting an interaction between a protein containing an SH2 domain and a phophotyrosine-containing polypeptide.

8 Claims, 10 Drawing Sheets

OTHER PUBLICATIONS

Schlessinger, J., (1993), "How receptor tyrosine kinases activates Ras", *Trends Biochem. Sci.,* vol. 18, pp. 273–275.

Tsukada, S., et al., (1993), "Deficient Expression of a B Cell Cytoplasmic Tyrosine Kinase in Human X–Linked Agammaglobulinemia", *Cell,* vol. 72, pp. 279–290.

Ahmad, S., (1993), "A widely expressed human protein–tyrosine phosphatase containing src homology 2 domain", *Proceedings of the National Academy of Sciences,* vol. 90, pp. 2197–2201.

David, M., et al., (1993), "*In Vitro* Activation of the Transcription Factor ISGF3 by Interferon α Involves a Membrane–associated Tyrosine Phosphatase and Tyrosine Kinase", *The Journal of Biological Chemistry,* vol. 268, No. 9, pp. 6593–6599.

Igarshi, K., et al., (1993), "In Vitro Activation of the Transcription Factor Gamma Interferon Activation Factor by Gamma Interferon: Evidence for a Tyrosine Phosphatase/Kinase Signaling Cascade", *Molecular and Cellular Biology,* vol. 13, No. 3, pp. 1634–1640.

Feig, L. A., (1993), "The Many Roads That Lead to Ras", *Science,* vol. 260, pp. 767–768.

Rudd, C. E., et al. (1993), "src–related protein tyrosine kinases and their surface receptors", *Biochimica et Biophysica Acta,* vol. 1155, pp. 239–266.

Cambier, J. C. and Cambell, K. S., (1992), "Membrane immunoglobulin and its accomplices: new lessons from an old receptor", *The FASEB Journal,* vol. 6, pp. 3207–3217.

Cantley, L. C., et al., (1991), "Oncogenes and Signal Transduction", *Cell,* vol. 64, pp. 281–302.

Evans, B. E., et al., (1988), "Methods for Drug Discovery: Development of Potent, Selective, Orally Effective Cholecystokinin Antagonists", *J. Med. Chem.,* vol. 31, pp. 2235–2246.

Bock, M. G., et al., (1987), "An Expedient Synthesis of 3–Amino–1, 3–Dihydro–5–Phenyl–2H–1, 4–Benzodiazepin–2–One", *Tetrahedron Letters,* vol. 28, No. 9, pp. 939–942.

Evans, B. E., et al., (1987), "Design of Non peptidal Ligands for a Peptide Receptor: Cholecystokinin Antagonists", *J. Med. Chem.,* vol. 30, pp. 1229–1239.

Bock, M. G., et al., (1987), "Synthesis and Resolution of 3–Amino–1, 3–Dihydro–5–Phenyl–2H–1, 4–Benzodiazepin–2–ones", *J. Org. Chem.,* vol. 52, pp. 3232–3239.

Chang, R. S. L. and Lotti, V. J., (1986), "Biochemical and pharmacological characterization of an extremely potent and selective nonpeptide cholecystokinin antagonist", *Proceedings of the National Academy of Sciences,* vol. 83, pp. 4923–4926.

Hirai, K., et al., (1980), "Peptidoaminobenzophenones, a Novel Class of Ring–Opened Derivatives of 1,4–Benzodiazephines", *J. Med. Chem.,* vol. 23, pp. 764–773.

Freidinger, R. M., (1987), "Design and comparison of nonpeptide and peptide CCK antagonists", *Peptides Chemistry and Biology Proceedings of the Tenth American Peptide Symposium,* May 23–28, pp. 97–100.

PHOSPHOTYROSINE PEPTIDOMIMETICS FOR INHIBITING SH2 DOMAIN INTERACTIONS

BACKGROUND OF THE INVENTION

Many of the physiological activities of a cell are controlled by external signals that stimulate or inhibit intracellular events. The process by which an external signal is transmitted into and within a cell to elicit an intracellular response is referred to as signal transduction. Signal transduction is generally initiated by the interaction of extracellular factors (For example, hormones, adhesion molecules, cytokines, and the like) with membrane receptors on the cell surface. These extracellular signals are transduced to the inner face of the cell membrane, where the cytoplasmic domains of receptor molecules make contact with intracellular targets. The initial receptor-target interactions stimulate a cascade of additional molecular interactions involving multiple intracellular pathways that disseminate the signal throughout the cell. These complex, branching pathways coordinate the multifunctional cellular programs that trigger changes in cell behavior. The orchestration of diverse proteins in finely tuned intracellular pathways appears to require transient "comparmentalization" of the proteins into complexes. Through a series of inducible and reversible protein-protein interactions, regulatory proteins are recruited from soluble cell material to form short-lived protein complexes that relay signals throughout the cell.

The structural nature of these protein interactions is emerging through the identification of the individual proteins that participate in each signal transduction pathway, the elucidation of the temporal order in which these proteins interact, and the definition or the sites of contact between the proteins. X-ray crystallography and nuclear magnetic resonance (NMR) spectroscopy studies have provided detailed structural information on a few of these interactive protein domains.

Many of the proteins involved in signal transduction consist of multiple domains, some of which have enzymatic activity and some of which bind to other cellular proteins, DNA regulatory elements, calcium, nucleotides, or lipid mediators. The discovery that Src homology 2 (SH2) domains provide phosphorylation-dependent and sequence-specific contacts for assembly of receptor signaling complexes has provided a breakthrough in understanding signal transduction (Cantley et al., (1991 ) *Cell* 64:281–302; Koch et al. (1991 ) *Science* 252:668–674).

Src homology 2 (SH2) domains were first identified from sequence similarities in the noncatalytic regions of Src-related tyrosine kinases, spanning approximately 100 amino acid residues (Sadowski et al. (1986) *Mol. Cell. Biol.* 6:4396–4408). The subsequent discovery that SH2 domains bind to specific phosphorylated tyrosine residues has provided a link between tyrosine kinases and proteins that respond to tyrosine phosphorylation (for reviews see Koch et al. (1991) *Science* 252:668–674; Pawson and Gish, (1992) *Cell* 71:359–362; Mayer and Baltimore, (1993) *Trends Cell Biol.* 3:8–13). Now a vast number of proteins likely to be involved in signaling have been shown to contain SH2 domains. The transmission of growth factor-mediated signals, for example, depends critically on the sequence-specific recognition of phosphorylated tyrosines by SH2 domains, which have been discovered in a number of proteins that act downstream of growth factor receptors, including Ras GTPase-activating protein (GAP), phosphatidylinositol 3'-kinase (PIK), and phospholipase C-γ (reviewed by Cantley et al. (1991) *Cell* 64:281–302). SH2 domains serve to localize these proteins to activated receptors and are implicated in the modulation of enzymatic activity (O'Brien et al. (1990) *Mol. Cell. Biol.* 10:2855–2862; Roussel et al. (1991) *Proc. Natl. Acad. Sci. USA* 88:10696–10700; Backer et al. (1992) *EMBO J.* 11:3469–3479).

While SH2 domains share the common property of binding phosphotyrosine-containing peptides, additional biological specificity resides in the sequence contexts of the phosphotyrosine. Evidence that the binding of a particular SH2 domain to tyrosine-phosphorylated proteins is dependent on the primary sequence around the phosphotyrosine (pTyr) came from a comparison of the sequences of the regions of polyoma middle T and the platelet-derived growth factor (PDGF) receptor that bind phosphatidylinositol 3-kinase (Cantley et al. (1991) *Cell* 64:281–302). The sequence pTyr-X-Met was found at sites known to be critical for phosphatidylinositol-3-kinase binding to these proteins (Cohen et al. (1990) *Proc. Natl. Acad. Sci.* 87:4458–4462; Kazlauskas and Cooper, (1989) *Cell* 58:1121–1133; Talmage et al. (1989) *Cell* 59:55–65; Whitman et al. (1985) *Nature* 315:239–242), and this sequence has been predicitve for other receptors or receptor substrates that bind phosphatidylinositol-3-kinase (Lev et al. (1992) *Proc. Natl. Acad. Sci.* 89:678–682; McGlade et al. (1992) *Mol. Cell Biol.* 12:991–997; Sun et al. (1991) *Nature* 352–77; Reedijk et al. (1992) *EMBO J.* 11:1365–1372). Synthetic phosphopeptides based on this sequence have been found to block phosphatidylinositol 3-kinase binding to the PDGF receptor (Escobedo et al. (1991) *Mol. Cell. Biol.* 11:1125–1132; Fantl et al. (1992) *Nature* 352:726–730) and to polyoma middle T (Auger et al. (1992) *J. Biol. Chem.* 267:5408–5415; and Yoakim et al. (1992) *J. Virol.* 66:5485–5491). In addition, mutational studies have shown that the SH2 domains of phosphatidylinositol 3-kinase, Ras GAP, and PLC-γ recognize distinct phosphopeptide sequence in the PDGF receptor (Fantl et al. (1992) *Cell* 69:413–423; Kazlauskas et al. (1990) *Science* 247:1578–1581; (1992) *Mol. Cell Biol.* 12:2534–2544).

SUMMARY OF THE INVENTION

The present invention makes available novel compounds useful for inhibiting an interaction between a protein containing an SH2 domain and a phophotyrosine-containing polypeptide. In one aspect of the invention, the subject compunds are represented by the general formula α-amino-N[1-(2-AA-2-oxoethyl)-1-azepin-3-yl]-PTyr (Formula I), wherein PTyr represents a phosphotyrosine or a phosphotyrosine analog which is carboxy-terminally linked with a 3-amino moiety of the azepine, and AA represents a peptide or single amino acid residue amino-terminally linked through a peptide bond with the 2-oxoethyl moiety of the azepine. The azepine core mimics a dipeptidyl amide backbone, and the Ptyr, the azepine, and the AA together form a peptidyl analog of the general formula PTyr-Xaa-Xaa-AA.

In certain embodiments of the present invention, PTyr can further include an additional amino acid residue or peptide, or similar azepine moiety, linked in a peptidyl bond to the N-terminus of the phosphotyrosine in order to further extend the peptidomimetic amino terminally.

The phosphotyrosine moiety, pTyr, can be represented by the general formula

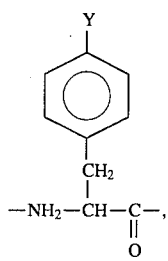

where Y is selected from a group consisting of

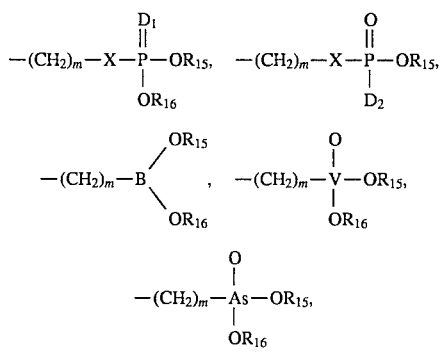

—$(CH_2)_m$—$BeF_3$, and —$(CH_2)_m$—$AlF_3$
wherein m is zero or an integer in the range of 1 to 6; X is absent or represents O, S, or N; $D_1$ represents O, or S; $D_2$ represents $N_3$, $SH_2$, $NH_2$, or $NO_2$; and $R_{15}$ and $R_{16}$ each independently represent hydrogen, a lower alkyl, or a pharmaceutically acceptable salt, or $R_{15}$ and $R_{16}$ taken together with the O—P—O, O—B—O, O—V—O or O—As—O atoms to which they are attached complete a heterocyclic ring having from 5 to 8 atoms in the ring structure. In a preferred embodiment, pTyr is a non-hydrolyzable phosphotyrosine analog.

In certain embodiments, the azepine is preferably a 1,4-diazepine, such as a 1,4-benzodiazepine. For instance, the compound can be a derivative of a 3-amino-1-(2-oxoethyl)-1,4-benzodiazepin-2-one, where the phosphotyrosine analog is covalently attached to the benzodiazepine by an amide bond with the 3-amino moiety, and the amino acid residue (or peptide) AA is attached to the benzodiazepine by an amide bond with said 1-oxoethyl moiety. In other embodiments, the peptidomimetic can be synthesized having a 1-azepine core, such as a 1-benzoazepine or a 1-pyridinoazepine.

The subject peptidomimetics, by selectively binding to a phosphotyrosine binding site of an SH2 domain, can be used to inhibit binding of a protein containing said SH2 domain with a phosphotyrosine residue of a target phosphoprotein. It is thus another aspect of the present invention to utilize the subject peptidomimetics to modulate intracellular signaling pathways by disrupting particular protein-protein interactions mediated by SH2 domains. For instance, the SH2 inhibitors of the present invention can be used to affect the responsiveness of a cell to a growth factor, cytokine or other receptor ligand; as an immunosuppressant; to prevent osteoclastic resorption of bone during osteoporosis; influence differentiation of cells; to modulate cellular response to interactions with the extracellular matrix, as well as affect the production and secretion of extracellular matrix components; prevent viral infection and/or viral-mediated transformation of cells; and to inhibit the proliferation of transformed cells or to render transformed cells more sensitive to cytostatic or cytotoxic agents. The SH2 target of the subject inhibitors can range from the interaction between, for example, an activated receptor complex and the initial cytoplasmic proteins involved in triggering a particular set of intracellular signaling pathways, to the last SH2-mediated interaction in a specific pathway, such as the formation of a transcription factor complex or allosteric regulation of an enzymatic activity. Thus, the inhibitors of the present invention can be used to prevent the interaction between a phosphotyrosine residue and such SH2-containing signal transduction proteins as, for example, Src, Lck, Fps, phosphatidylinositol-3-kinases, ras GTPase-activating protein, Fyn, Lyk, Fgr, Fes, ZAP-70, Abl, Crk, Nck, Sem-5, p85, phospholipase C, SHPTP1, SHPTP2, corkscrew, Syk, Lyn, Yes, Hck, Dsrc, Tec, Atk/Bpk, Itk/Tsk, Arg, Csk, tensin, Vav, Shc, Emt, Grb2, Syp, Blk, Bpk 113TF, 91TF, and Janus kinases including Tyk2, JAK1 and JAK2.

DETAILED DESCRIPTION OF THE INVENTION

Figure 1A:
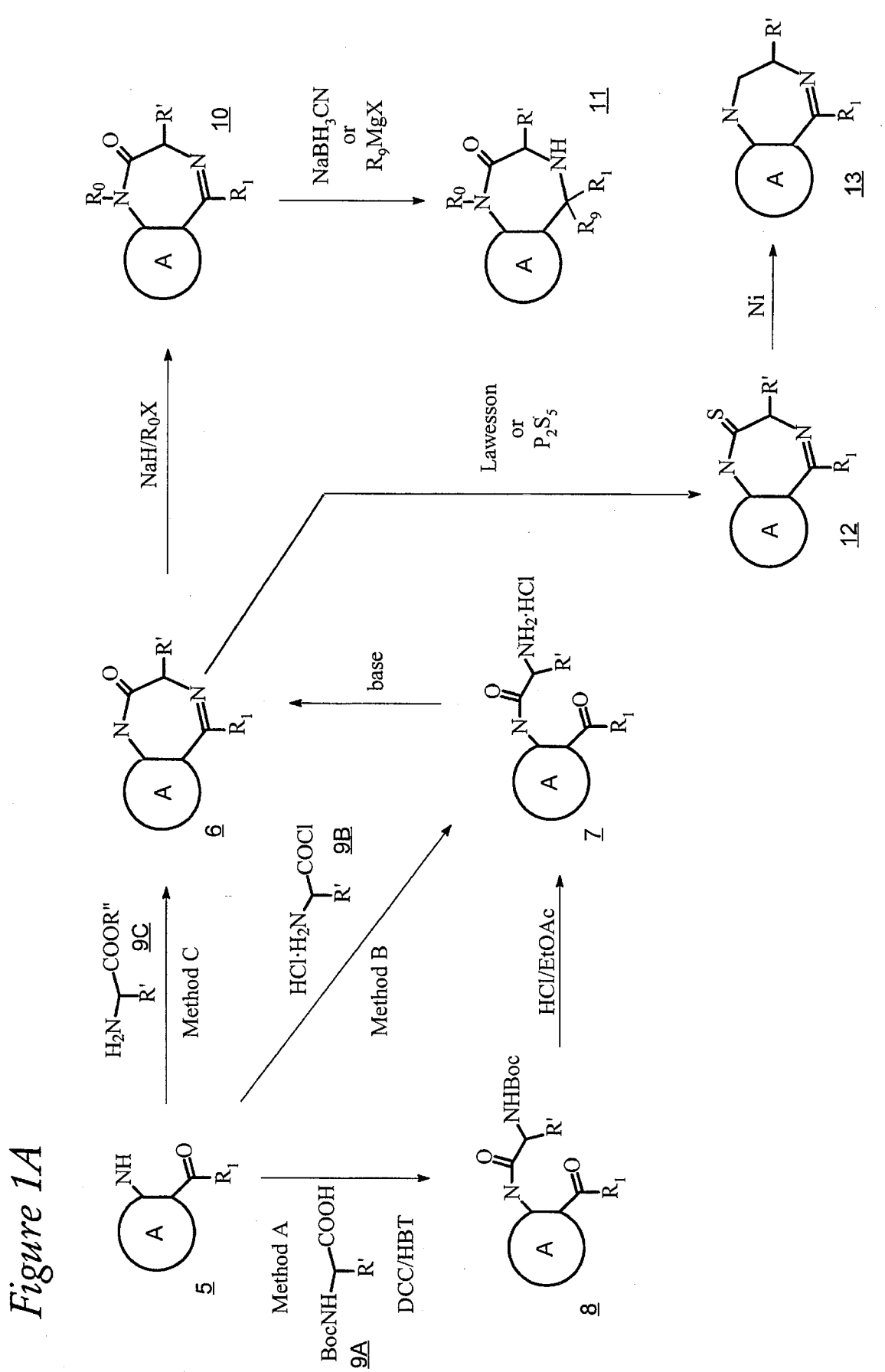
FIGS. 1A, 1B and 1C illustrate general reaction schemes for generating the subject peptidomimetics having 1,4-diazepine cores.

Protein-protein interactions are involved in all stages of the intracellular signal transduction process -at the plasma membrane, where the signal is initiated in the cytoplasm by receptor recruitment of other cellular proteins; in the cytoplasm, where the signals are disseminated to different cellular locations; and in the nucleus, where other proteins involved in transcriptional control form complexes to regulate transcription of particular genes. Accumulating evidence suggests that selected sequences surrounding tyrosine phosphorylation sites can be recognized by proteins containing srcohomology 2 (SH2) domains, and that such phosphotyrosine recognition functions to propagate intracellular signals by mediating the formation and/or dissolution of protein complexes. Phosphoprotein recognition by SH2 domain-containing proteins is thought to derive its specificity from the presence of a phosphorylated tyrosine as well as from the surounding amino acid sequence.

The present invention makes available novel peptidomimetics useful for inhibiting an interaction between a protein containing an SH2 domain and a phophotyrosine-containing polypeptide. In one aspect of the invention, the subject peptidomimetic is represented by the general formula α-amino-N-[1-(2-AA-2-oxoethyl)-1-azepin-3-yl]-PTyr (Formula I), wherein PTyr represents a phosphotyrosine or a phosphotyrosine analog which is carboxy-terminally linked with a 3-amino moiety of the azepine, and AA represents a peptide or single amino acid residue aminoterminally linked through a peptide bond with the 2-oxoethyl moiety of the azepine. The azepine core mimics a dipeptidyl amide backbone, and the PTyr, the azepine, and the AA together form a peptidyl analog of the general formula PTyr-Xaa-Xaa-AA. In certain embodiments of the present invention, PTyr can further include an additional amino acid residue or peptide, or similar azepine moiety, linked in a peptidyl bond to the N-terminus of the phosphotyrosine in order to further extend the peptidomimetic amino terminally.

In an exemplary embodiment, the peptidyl-azepine is represented by a Formula II:

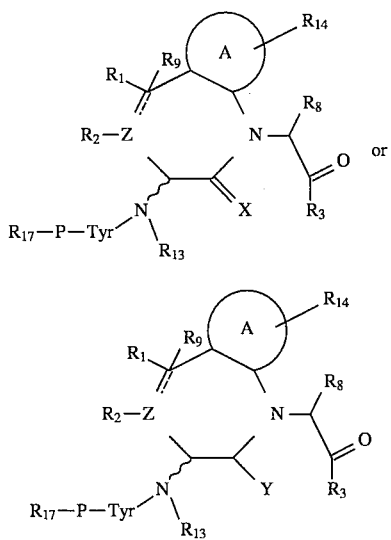

wherein

A represents a fused ring selected from a group consisting of a cycloalkyl, a cycloakenyl, an aryl, and a heterocyclic ring, wherein the fused ring A can comprise from 4 to 8 atoms in its ring structure, and can also be substituted or unsubstituted;

$R_1$ represents hydrogen, a halogen, a lower alkyl, a lower alkenyl, a lower alkynyl, a carboxyl, an azido, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_m$—SH, —$(CH_2)_m$—S-lower alkyl, —$(CH_2)_m$—S-lower alkenyl, —$(CH_2)_n$—S—$(CH_2)_m$—$R_7$,

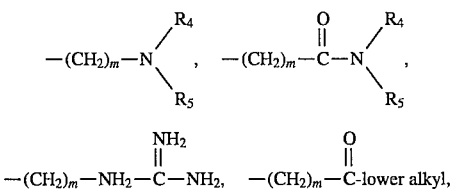

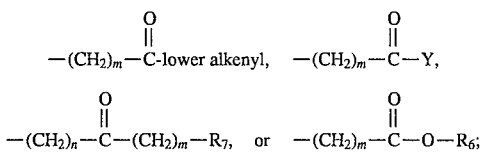

$R_2$ represents an electron lone pair, hydrogen, an lower alkyl, an lower alkenyl, an lower alkynyl, a carboxyl, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_p$—SH, —$(CH_2)_p$—S-lower alkyl, —$(CH_2)_p$—S-lower alkenyl, —$(CH_2)_p$—S—$(CH_2)_m$—$R_7$,

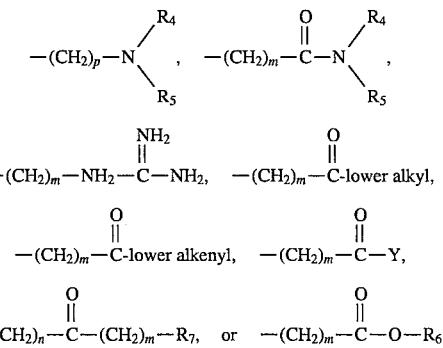

$R_3$ represents an N-terminally linked amino acid residue or peptide;

$R_4$ and $R_5$ each independently represent hydrogen, lower alkyl, lower alkenyl, —$(CH_2)_m$—$R_7$, —C(O)-lower alkyl, —C(O)-lower alkenyl, —C(O)—$(CH_2)_m$—$R_7$, or $R_4$ and $R_5$ taken together with the N atom to which they are attached complete a heterocyclic ring having from 4 to 8 atoms in the ring structure;

$R_6$ represents hydrogen, a lower alkyl, a lower alkenyl, $R_7$, —$(CH_2)_p$—$R_7$, or a pharmaceutically acceptable salt forming ion;

$R_7$ represents an aryl, a cycloalkyl, a cycloakenyl, or a heterocycle;

$R_8$ represents hydrogen, a halogen, a lower alkyl, a lower alkenyl, a lower alkynyl, a carboxyl, an azido, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_m$—SH, —$(CH_2)_m$—S-lower alkyl, —$(CH_2)_m$—S-lower alkenyl, —$(CH_2)_n$—S—$(CH_2)_m$—$R_7$,

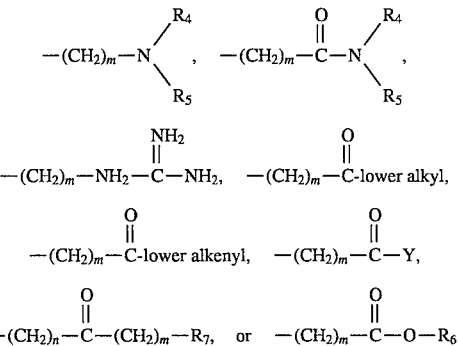

$R_9$ is absent, hydrogen, or a lower alkyl;

$R_{13}$ represents hydrogen, or a lower alkyl;

$R_{14}$ is absent or represents a halogen, a lower alkyl, a lower alkoxy, a lower alkylthio, —$NO_2$, —$CF_3$, —CN, and —OH;

$R_{17}$ is absent or represents a C-terminally linked amino acid residue or peptide;

X represents O or S; Y represents hydrogen, a lower alkyl, $-(CH_2)_m-OH$, $-(CH_2)_m-O-$lower alkyl, a carboxyl, an amine, an amide, a nitrosyl, a sulfhydryl, a sulfonyl, or a sulfonamide;

Z represents C or N;

P-Tyr represents a phosphotyrosine, or a phosphotyrosine analog, the carboxyl group of said phosphotyrosine being linked by an amide bond to the 3-amino group of said azepine;

n is zero or an integer in the range of 1 to 6; m is zero or an integer in the range of 1 to 6; and p is an integer in the range of 1 to 6.

Moreover, the subject peptidomimetic can be tethered to form polymers, preferably homodimers or heterodimers. Such molecules can be useful to, for example, bring two or more SH2 containing proteins into proximity. Alternatively, the specificity of the peptidomimetic can be increased in a manner analogous to antibody avidity, by virtue of its ability to bind two SH2 domains on the same protein, be they similar or dissimilar in specificity. Thus, the tethers can be formed, as for instance, any one of the sidechains $R_1$, $R_2$, $R_8$, $R_9$, or $R_{14}$ being a covalent bridge between two or more azepine cores.

As used herein, the definition of each expression, e.g. lower alkyl, m, n, p, etc., when it occurs more than once in any structure, is intended to be independent of its definition elsewhere in the same structure.

In preferred embodiments, the fused ring A is selected from a group consisting of benzene, pyrrole, furan, thiphene, imidazole, oxazole, thiazole, triazole. pyrazole, pyrroine, pyridine, pyrazine, pyridazine and pyrimidine, and the like. The fused ring A can be substituted, for example, by any of a halogen, a lower alkyl, a lower alkoxy, a lower alkylthio, $-NO_2$, $-CF_3$, $-CN$, and $-OH$. Though it will be understood that in some instances it may be undesirable to have a substituent, such as a halogen or a nitro group, in the 7 position (particularly wherein A is a benzyl ring) as such substituents are generally required for sedative-hypnotic activity in other benzodiazpines, such as daizepam or nitrazepam.

Likewise, in preferred, yet optional, embodiments, $R_1$ is particularly selected from a group consisting of $-(CH_2)_m$-benzyl, $-(CH_2)_n-S-(CH_2)_m$-benzyl, $-(CH_2)_n-O-(CH_2)_m$-benzyl, $-(CH_2)_m$-pyridyl, $-(CH_2)_n-S-(CH_2)_m$-pyridyl, and $-(CH_2)_n-O-(CH_2)_m$-pyridyl. Additionally, each of the benzyl and pyridyl moieties can be substituted at one or more positions with a halogen, a lower alkyl, a lower alkoxy, a lower alkylthio, $-NO_2$, $-CF_3$, $-CN$, and $-OH$. The choice of $R_1$, as well as the other substituents of the azepine peptidomimetic, can effect the solubulity, as well as membrane partioning of the subject peptidomimetics. For instance, as a result of their pyridyl-substituted nature, pyridyl containing $R_1$ substituents can exhibit a greater water solubility than the analogous benzyl-substituted azepines.

In illustrative embodiments, $R_3$ can be an amino acid selected from a group consisting of leucine, isoleucine, methionine, proline, valine, aspartic acid, and asparagine. These exemplary peptidomimetic agents can be used to inhibit the phosphotyrosine binding of such SH2 domain-containing proteins as Src, Lck, Fps, phosphatidylinositol-3-kinases, ras GTPase-activating protein, Fyn, Lyk, Fgr, Fes, ZAP-70, Abl, Crk, Nck, Sem-5, p85, phospholipase C, SHPTP1, SHPTP2, corkscrew, Syk, Lyn, Yes, Hck, Dsrc, Tec, Atk/Bpk, Itk/Tsk, Arg, Csk, tensin, Vav, Shc, Emt, Grb2, Syp, Blk, Bpk 113TF, 91TF, and Janus kinases including Tyk2, JAK1 and JAK2.

The term "alkyl" is recognized in the art and refers to saturated aliphatic groups having one to ten carbon atoms, including straight-chain alkyl groups, branched-chain alkyl groups, cycloalkyl (alicyclic) groups, alkyl substituted cycloalkyl groups, and cycloalkyl substituted alkyl groups. Such hydrocarbon moieties may be substituted on one or more carbons with, for example, a halogen, a hydroxyl, a thiol, an amino, or a nitro group. In the instance of the cycloalkyls, such substituents can further comprise a lower alkyl, a lower alkenyl, a lower alkoxy, a lower alkylthio, a lower alkylamino, a lower alkylcarboxyl, a nitro, a hydroxyl, $-CF_3$, $-CN$, or the like. Unless the number of carbons is otherwise specified, "lower alkyl" as used herein means an alkyl group, as defined above, but having from one to six carbon atoms, rather than from one to ten carbon atoms. Representative of such alkyl groups are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "amino" means $-NH_2$; the term "nitro" means $-NO_2$; the term "halogen" designates $-F$, $-Cl$, $-Br$ or $-I$; the term "thiol" means $SH_2$; and the term "hydroxyl" means $-OH$. Thus, the term "alkylamino" as used herein means an alkyl group, as defined above, having an amino group attached thereto. The term "alkylthio" refers to an alkyl group, as defined above, having a sulphydryl group attached thereto. The term "alkylcarboxyl" as used herein means an alkyl group, as defined above, having a carboxyl group attached thereto. The term "alkoxy" as used herein means an alkyl group, as defined above, having an oxygen atom, attached thereto. Representative alkoxy groups include methoxy, ethoxy, propoxy. tert-butoxy and the like.

The terms "alkenyl" and "alkynyl" refer to unsaturated aliphatic groups analogous to alkyls, but which contain at least one double or triple bond respectively.

The terms "oxoethyl" and "carbonylmethyl" refer to the general structure

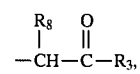

wherein $R_8$ and $R_3$ are as defined above.

The term "aryl" as used herein includes 4-, 5- and 6-membered single-ring aromatic groups which may include from zero to four heteroatoms, for example, benzene, pyrrole, furan, thiphene, imidazole, oxazole, thiazole, triazole, pyrazole, pyrroine, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, $-CF_3$, $-CN$, or the like.

The term "heterocycle" or "heterocyclic group" refers to 4-, 5- and 6- membered single-ring alicyclic groups which include one to four heteroatoms. Heterocyclic groups include pyrrolidine, oxolane, thiolane, imidazolidine, oxazolidine, piperidine, piperazine, morphaline. The alicyclic ring can be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, $-CF_3$, $-CN$, or the like.

The phrase "fused ring" is art recognized and refers to a cyclic moiety which can comprise from 4 to 8 atoms in its ring structure, and can also be substituted or unsubstituted, (e.g., cycloalkyl, a cycloakenyl, an aryl, or a heterocyclic ring) that shares a pair of carbon atoms with the azepine core. For example, in the structure

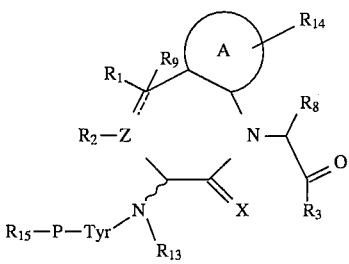

both A and the azepine together form a fused ring system. To illustrate, the fused ring system can be a benzodiazepine, a benzoazepine, a pyrrolodiazepine, a pyrroloazepine, a furanodiazepine, a furanoazepine, a thiphenodiazepine, a thiphenoazepine, an imidazolodiazepine, an imidazoloazepine, an oxazolodiazepine, an oxazoloazepine, a thiazolodiazepine, a thiazoloazepine, a pyrazolodiazepine, a pyrazoloazepine, a pyrazinodiazepine, a pyrazinoazepine, a pyridinodiazepine, a pyridinoazepine, a pyrimidinodiazepine, and a pyrimidinoazepine.

The term "heteroatom" as used herein means an atom of any element other than carbon or hydrogen. Preferred heteroatoms are nitrogen, oxygen, sulpher and selenium.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see *Biochemistry* (1972) 11:1726–1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, *"Peptides and Amino Acids"*, W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H-(the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term amino acid residue further includes analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject peptidomimetic can include an amino acid analog as for example, β-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention.

Also included are the D and L stereoisomers of such amino acids when the structure of the amino acid admits of stereoisomeric forms. The configuration of the amino acids and amino acid residues herein are designated by the appropriate symbols D, L or DL, furthermore when the configuration is not designated the amino acid or residue can have the configuration D, L or DL. It will be noted that the structure of some of the compounds of this invention includes asymmetric carbon atoms. It is to be understood accordingly that the isomers arising from such asymmetry are included within the scope of this invention. Such isomers are obtained in substantially pure from by classical separation techniques and by sterically controlled synthesis and have arbitrarily been named, for example, as isomers #1 or #2. For the purposes of this application, unless expressly noted to the contrary, a named amino acid shall be construed to include both the D or L stereoisomers, preferably the L stereoisomer.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, carbonylbenzyloxy (Cbz); and aliphatic urethane protecting groups such as t-butyloxycarbonyl (Boc) or 9-Fluorenylmethoxycarbonyl (FMOC). Peptidomimetics of the present invention which have sidechain or azepine ring substituents which include amino groups -such as where R$_3$ is a lysine or arginine, or where R$_8$, R$_1$, R$_2$ or Y comprise a free amino group- can optionally comprise suitable N-terminal protecting groups attached to the sidechains.

The phrase "C-terminal protecting group" or "carboxyl-protecting group" as used herein refers to those groups intended to protect a carboxylic acid group. such as the C-terminus of an amino acid or peptide or an acidic or hydroxyl azepine ring substituent, against undesirable reactions during synthetic procedures and includes. Benzyl or other suitable esters or ethers are illustrative of C-terminal protecting groups known in the art.

The terms "phosphotyrosine" and "phosphotyrosine analog", for ease of reading, appear interchangably as a portion of the formula representing the subject peptidomimetics. As used herein, with respect to the appearance in a formula for the present compounds, either term is intended to encompass any phosphotyrosine analog of the general formula:

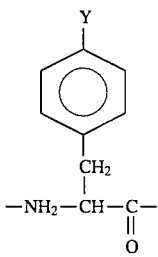

in which Y is a phosphate group or phosphate analog. In preferred embodiments, Y is a non-hydrolyzable phosphate analog which is stable under normal physiological conditions. Exemplary choices for the phosphate analog Y include phenylalanine ring substituents represented by the general formulas

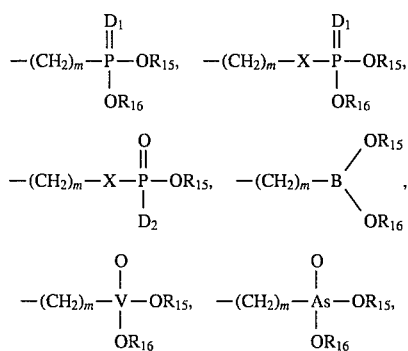

—(CH$_2$)$_m$—BeF$_3$, and —(CH$_2$)$_m$—AlF$_3$ wherein m is zero or an integer in the range of 1 to 6; X represents O, S, or N; D$_1$ represents O or S; D$_2$ represents N$_3$, SH$_2$, NH$_2$ or NO$_2$; and R$_{15}$ and R$_{16}$ each independently represent hydrogen, a lower alkyl, or a pharmaceutically acceptable salt, or R$_{15}$ and R$_{16}$ taken together with the O—P—O, O—B—O, O—V—O, or O—As—O atoms to which they are attached complete a heterocyclic ring having from 5 to 8 atoms in the ring structure. In preferred embodiments, R$_{15}$ and R$_{16}$ are capable of being hydrolysed to a hydroxyl group, particularly in aqueous solution at physiological pH.

In an exemplary embodiment, the peptidomimetic of the present invention is a benzodiazepine represented by the general formula (formula III):

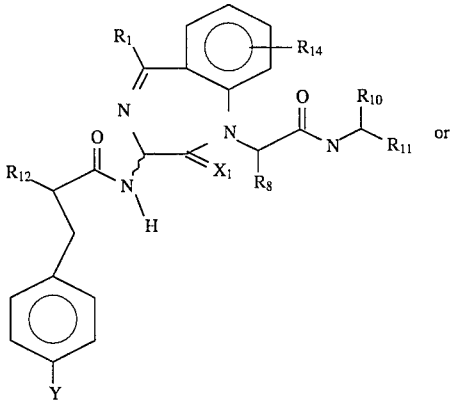

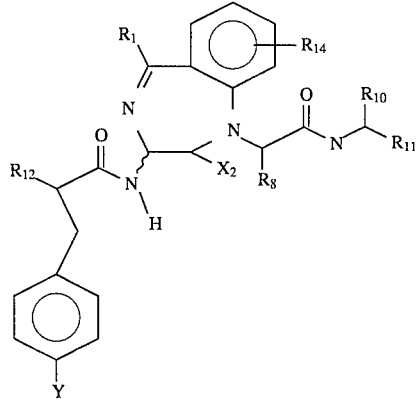

wherein

R$_1$ represents hydrogen, a halogen, a lower alkyl, a lower alkenyl, a lower alkynyl, a carboxyl, an azido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$R$_7$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_7$,

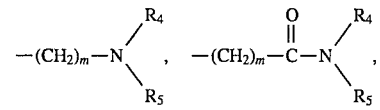

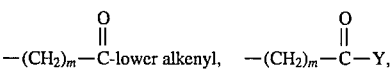

R$_4$ and R$_5$ each independently represent hydrogen, lower alkyl, lower alkenyl, —(CH$_2$)$_m$—R$_7$, —C(O)-lower alkyl, —C(O)-lower alkenyl, —C(O)—(CH$_2$)$_m$—R$_7$, or R$_4$ and R$_5$ taken together with the N atom to which they are attached complete a heterocyclic ring having from 4 to 8 atoms in the ring structure;

R$_6$ represents hydrogen, a lower alkyl, an lower alkenyl, —(CH$_2$)$_m$—R$_7$, or a pharmaceutically acceptable salt forming ion;

R$_7$ represents an aryl, a cycloalkyl, a cycloakenyl, or a heterocycle;

R$_8$ represents hydrogen, a halogen, a lower alkyl, a lower alkenyl, a lower alkynyl, a carboxyl, an azido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_7$,

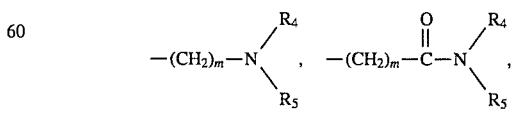

-continued

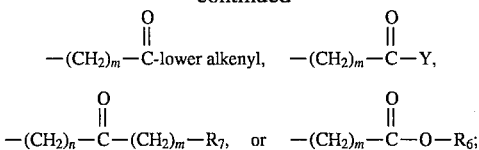

$R_{10}$ represents an alpha-carbon sidechain of an amino acid residue or analog thereof;

$R_{11}$ represents COOH or a pharmaceutically acceptable salt thereof, or a carboxy-terminal blocking group;

$R_{12}$ represents $NH_2$ or a pharmaceutically acceptable salt thereof, an amino-terminal blocking group, or —NH—$R_{17}$;

$R_{14}$ represents a halogen, a lower alkyl, a lower alkoxy, a lower alkylthio, —$NO_2$, —$CF_3$, —CN, and —OH;

$R_{17}$ represents a C-terminally linked amino acid residue or peptide;

Y represents a phosphate or phosphate analog;

$X_1$ represents O or S; $X_2$ represents hydrogen, a lower alkyl, —$(CH_2)_m$—OH, —$(CH_2)_m$—O-lower alkyl, a carboxyl, an amine, an amide, a nitrosyl, a sulfhydryl, a sulfonyl, or a sulfonamide;

n is zero or an integer in the range of 1 to 6; m is zero or an integer in the range of 1 to 6; and p is an integer in the range of 1 to 6.

For instance, the peptidomimetic can be a 5-benzyl substituted 1,4-diazepine represented by the general formula (formula IV):

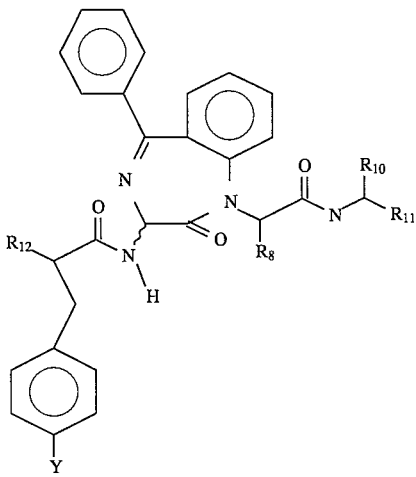

wherein $R_8$ represents hydrogen or an amino acid sidechain; $R_{10}$ represents an alpha-carbon sidechain of an amino acid residue or amino acid analog; $R_{11}$ represents COOH or a pharmaceutically acceptable salt thereof, or a carboxy-terminal blocking group; $R_{12}$ represents $NH_2$ or a pharmaceutically acceptable salt thereof, or an amino-terminal blocking group; and Y represents a phosphate or phosphate analog.

In preferred, though exemplary embodiments, the subject compound is represented by one of the following formulas:

(1) 1,3-Dihydro-1-[(L-isoleucyl)-carbonylethyl)-5-phenyl-3(R,S)-{[(N-acetyl)-phosphono-L-tyrosyl]amino}-2H-1,4-benzodiazepin-2-one (2) 1,3-Dihydro-1-[(L-methionyl)-carbonylmethyl)-5-phenyl-3(R,S)-{[(N-acetyl)-phosphono-L-tyrosyl]amino}-2H-1,4-benzodiazepin-2-one (3) 1,3-Dihydro-1-[(L-leucyl)-carbonylmethyl)-5-phenyl-3(R,S)-{[(N-acetyl)-phosphono-L-tyrosyl]amino}-2H-1,4-benzodiazepin-2-one (4) 1,3-Dihydro-1-[(L-prolyl)-carbonylmethyl)-5-phenyl-3(R,S)-{[(N-acetyl)-phosphono-L-tyrosyl]amino}-2H-1,4-benzodiazepin-2-one (5) 1,3-Dihydro-1-[(L-valyl)-carbonylmethyl)-5-phenyl-3(R,S)-{[(N-acetyl)-phosphono-L-tyrosyl]amino}-2H-1,4-benzodiazepin-2-one (6) 1,3-Dihydro-1-[(L-aspartyl)-carbonylmethyl)-5-phenyl-3(R,S)-{[(N-acetyl)-phosphono-L-tyrosyl]amino}-2H-1,4-benzodiazepin-2-one (7) 1,3-Dihydro-1-[(L-asparginyl)-carbonylmethyl)-5-phenyl-3(R,S)-{[(N-acetyl)-phosphono-L-tyrosyl]amino}-2H-1,4-benzodiazepin-2-one (8) 1,3-Dihydro-1-[(L-isoleucyl)-carbonylmethyl)-5-phenyl-3(R,S)-{[(N-acetyl)-4-boronylphenylalanine]amino}-2H-1,4-benzodiazepin-2-one (9) 1,3-Dihydro-1-[(L-methionyl)-carbonylmethyl)-5-phenyl-3(R,S)-{[(N-acetyl)-4-boronylphenylalanine]amino}-2H-1,4-benzodiazepin-2-one

(10) 1,3-Dihydro-1-[(L-leucyl)-carbonylmethyl)-5-phenyl-3(R,S)-{[(N-acetyl)-4-boronylphenylalanine]amino}-2H-1,4-benzodiazepin-2-one

(11) 1,3-Dihydro-1-[(L-prolyl)-carbonylmethyl)-5-phenyl-3(R,S)-{[(N-acetyl)-4-boronylphenylalanine]amino}-2H-1,4-benzodiazepin-2-one

(12) 1,3-Dihydro-1-[(L-valyl)-carbonylmethyl)-5-phenyl-3(R,S)-{[(N-acetyl)-4-boronylphenylalanine]amino}-2H-1,4-benzodiazepin-2-one

(13) 1,3-Dihydro-1-[(L-aspartyl)-carbonylmethyl)-5-phenyl-3(R,S)-{[(N-acetyl)-4-boronylphenylalanine]amino}-2H-1,4-benzodiazepin-2-one

(14) 1,3-Dihydro-1-[(L-asparginyl)-carbonylmethyl)-5-phenyl-3(R,S)-{[(N-acetyl)-4-boronylphenylalanine]amino}-2H-1,4-benzodiazepin-2-one

(15) 1,3-Dihydro-1-[(L-isoleucyl)-carbonylmethyl)-5-phenyl-3(R,S)-{[(N-acetyl)-4-arsenylphenylalanine]amino}-2H-1,4-benzodiazepin-2-one

(16) 1,3-Dihydro-1-[(L-methionyl)-carbonylmethyl)-5-phenyl-3(R,S)-{[(N-acetyl)-4-arsenylphenylalanine]amino}-2H-1,4-benzodiazepin-2-one

(17) 1,3-Dihydro-1-[(L-leucyl)-carbonylmethyl)-5-phenyl-3(R,S)-{[(N-acetyl)-4-arsenylphenylalanine]amino}-2H-1,4-benzodiazepin-2-one

(18) 1,3-Dihydro-1-[(L-prolyl)-carbonylmethyl)-5-phenyl-3(R,S)-{[(N-acetyl)-4-arsenylphenylalanine]amino}-2H-1,4-benzodiazepin-2-one

(19) 1,3-Dihydro-1-[(L-valyl)-carbonylmethyl)-5-phenyl-3(R,S)-{[(N-acetyl)-4-arsenylphenylalanine]amino}-2H-1,4-benzodiazepin-2-one

(20) 1,3-Dihydro-1-[(L-aspartyl)-carbonylmethyl)-5-phenyl-3(R,S)-{[(N-acetyl)-4-arsenylphenylalanine]amino}-2H-1,4-benzodiazepin-2-one

(21) 1,3-Dihydro-1-[(L-asparginyl)-carbonylmethyl)-5-phenyl-3(R,S)-{[(N-acetyl)-4-arsenylphenylalanine]amino}-2H-1,4-benzodiazepin-2-one

(22) 1,3-Dihydro-1-[(L-isoleucyl)-carbonylmethyl)-5-phenyl-3(R,S)-{[(N-acetyl)-4-phosphonomethylphenylalanine]amino}-2H-1,4-benzodiazepin-2-one

(23) 1,3-Dihydro-1-[(L-methionyl)-carbonylmethyl)-5-phenyl-3(R,S)-{[(N-acetyl)-4-phosphonomethylphenylalanine]amino}-2H-1,4-benzodiazepin-2-one

(24) 1,3-Dihydro-1-[(L-leucyl)-carbonylmethyl)-5-phenyl-3(R,S)-{[(N-acetyl)-4-phosphonomethylphenylalanine]amino}-2H-1,4-benzodiazepin-2-one

(25) 1,3-Dihydro-1-[(L-prolyl)-carbonylmethyl)-5-phenyl-3(R,S)-{[(N-acetyl)-4-phosphonomethylphenylalanine]amino}-2H-1,4-benzodiazepin-2-one

(26) 1,3-Dihydro-1-[(L-valyl)-carbonylmethyl)-5-phenyl-3(R,S)-{[(N-acetyl)-4-phosphonomethylphenylalanine]amino}-2H-1,4-benzodiazepin-2-one

(27) 1,3-Dihydro-1-[(L-aspartyl)-carbonylmethyl)-5-phenyl-3(R,S)-{[(N-acetyl)-4-phosphonomethylphenylalanine]amino}-2H-1,4-benzodiazepin-2-one
(28) 1,3-Dihydro-1-[(L-asparginyl)-carbonylmethyl)-5-phenyl-3(R,S)-{[(N-acetyl)-4-phosphonomethylphenylalanine]amino}-2H-1,4-benzodiazepin-2-one
(29) 1,3-Dihydro-1-[(L-isoleucyl)-carbonylmethyl)-5-phenyl-3(R,S)-{[(N-acetyl)-4-vanadylphenylalanine]amino}-2H-1,4-benzodiazepin-2-one
(30) 1,3-Dihydro-1-[(L-methionyl)-carbonylmethyl)-5-phenyl-3(R,S)-{[(N-acetyl)-4-vanadylphenylalanine]amino}-2H-1,4-benzodiazepin-2-one
(31) 1,3-Dihydro-1-[(L-leucyl)-carbonylmethyl)-5-phenyl-3(R,S)-{[(N-acetyl)-4-vanadylphenylalanine]amino}-2H-1,4-benzodiazepin-2-one
(32) 1,3-Dihydro-1-[(L-prolyl)-carbonylmethyl)-5-phenyl-3(R,S)-{[(N-acetyl)-4-vanadylphenylalanine]amino}-2H-1,4-benzodiazepin-2-one
(33) 1,3-Dihydro-1-[(L-valyl)-carbonylmethyl)-5-phenyl-3(R,S)-{[(N-acetyl)-4-vanadylphenylalanine]amino}-2H-1,4-benzodiazepin-2-one
(34) 1,3-Dihydro-1-[(L-aspartyl)-carbonylmethyl)-5-phenyl-3(R,S)-{[(N-acetyl)-4-vanadylphenylalanine]amino}-2H-1,4-benzodiazepin-2-one
(35) 1,3-Dihydro-1-[(L-asparginyl)-carbonylmethyl)-5-phenyl-3(R,S)-{[(N-acetyl)-4-vanadylphenylalanine]amino}-2H-1,4-benzodiazepin-2-one As noted above, certain peptidomimetics of the present invention may exist in particular geometric or stereoisomeric forms. The present invention contemplates all such compounds, including cis- and trans-isomers, R- and S-enantiomers, diastereomers, d-isomers, 1-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The pharmaceutical acceptable salts of the subject peptidomimetics include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the subject peptidomimetic which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject peptidomimtrics are also readily prepared by conventional procedures such as treating an acid of Formula I with an appropriate amount of a basera such as an alkali or alkaline earth metal hydroxide (e.g. sodium, potassium, lithium, calcium or magnesium) or an organic base such as an amine, piperidine, pyrrolodine, benzylamine and the like, or a quaternary ammonium hydroxide such as tetramethylammonium hydroxide and the like.

Contemplated equivalents of the compounds described in Formula I include compounds which otherwise correspond thereto, and which have the same general properties thereof (e.g. the ability to inhibit an SH2-phosphotyrosine interaction), wherein one or more simple variations of substituents are made which do not adversely affect the efficacy of the compound in inhibiting the interaction of an SH2 domain with a phosphotyrosine-containing polypeptide. In general, the peptidomimetics of the present invention may be prepared by the methods illustrated in the general reaction schemes shown in FIGS. 1–5, or by modifications thereof, using readily available starting materials, reagents and conventional synthesis procedures. In these reactions, it is also possible to make use of variants which are in themselves known, but are not mentioned here. Owing to their extensive use as antagonists of cholecystokinin, the synthesis of many variants of the azepine core structure, particularly of the benzodiazepines, is generally known in the art (see, for example, Evans et al. U.S. Pat. No. 4,820,834; Bock et al. U.S. Pat. No. 4,755,508; Freidinger et al. U.S. Pat. No. 5,206,237; Bock et al. U.S. Pat. No. 5,175,159; Bock et al. U.S. Pat. No. 4,628,084; Bock et al. (1987) *J. Org. Chem.* 52:3232–3239; Evans et al. (1988) *J. Med Chem.* 31:2235–246; Evans et al. (1987) *J. Med. Chem.* 30:1229–1239; Bock et al. (1987) *Tetrahedron* 8:939–949; Sternbach et al. (1962) *J Org Chem* 27:3788; Reider et al. (1987) *J Org Chem* 52:957; and Rodriquez et al. in *Peptides: Chemistry and Biology*, G. R. Marshall ed., ESCOM Publisher: Leiden, Netherlands, 1988).

In each of the reaction schemes resulting in 1,4-diazepine cores, a 2-aminocyclic ketone, shown generally as compound 5 in FIG. 1A, is used to generate the fused-ring diazepine core of the present peptide analogs. FIG. 1A, for example, illustrates the coupling of an amino acid analog to the 2-amino group of 5 by conventional peptide coupling techniques. In the preferred synthetic route of FIG. 1A, the aminocyclic ketone 5 is coupled to an N-protected amino acid 9A (such as a Boc-glycine or Boc-alanine) using dicyclohexylcarbodiimide (DCC) or other conventional peptide coupling reagent (method A). The product 8 is N-deprotected by treatment with acid, preferably anhydrous HCl in ethyl acetate in instances wherein the protecting group is a BOC protecting group, to give the α-aminoacyl derivative 7 of the aminocyclic ketone. An another route to synthesize 7 involves the basic synthetic approach (method B) of treating the ketone 5 with the amino acid chloride hydrochloride 9B, prepared from the amino acid with, for instance, $PCl_5$-AcCl.

Treatment of this aminoacyl derivative 7 with base, preferably aqueous sodium hydroxide in methanol, gives the free base, which can be subsequently cyclized to the 1,4-diazepine 6 upon stirring with methanolic base (Evans et al. (1987) *J Med Chem* 30: 1229–1239; and Evans et al. U.S. Pat. No. 4,820,834).

Alternatively, compound 6 can be obtained by heating the ketone 5 with the amino acid ester 9C, such as alanine or glycine methyl ester hydrochloride, in refluxing pyridine (method C; c.f. Evans et al. (1987) *J Med Chem* 30:1229–1239; and Sternbach et al. (1962) *J Org Chem* 27:3788).

The 3,5-disubstituted diazepine 6 can be treated with sodium hydride in dimethyl formamide (DMF), followed by an alkyl halide $R_0X$ (e.g., $R_0$=—CH(—$R_8$)—C(O)—$R_3$, or —CH(—$R_8$)—$CO_2tBu$), to yield the 1-alkyl derivative 10. This or the parent 1-unsubstituted compound 6 can be reduced to give the corresponding 4,5-dicyclo compounds 11, such as by treatment with sodium cyanoborohydride and acetic acid at 15° C. ($R_9$=H), or by treatment with alkyl magnesium halides (e.g. $R_9MgX$; $R_9$=a lower alkyl), such as methylmagnesium iodide, to produce a disubstituted $C_5$. Compound 11 can subsequently be alkylated on $N_4$ by treatment with an alkyl halide (e.g. $R_2X$) or dialkyl sulfate. Alternatively, the 4,5-dihydro compounds can be acylated on $N_4$ by treatment with acyl halides or anhydrides, preferably in the presence of base such as triethylamine.

The 2-thione 12 can be prepared from the parent amide (e.g., any of compounds 6, 10, or 11) by treatment with $P_2S_5$ or Lawesson's reagent (2,4-Bis-(4-methoxyphenyl)-2,4-dithioxo-1,3,2,4-dithiadi-phosphetane) according to published procedures (Scheibye et al. (1973) *Bull Soc Chim Belg.* 87:229). Desulfurization over Raney nickel of the thione 12 can be used to prepare the 2-unsubstituted diazepine 13. The latter may be alkylated with alkyl halide or sulfate, acylated with acylhalide or an hydride, reduced with sodium cyanoborohydride, or substituted with alkylmagnesium halide as described for 6 above.

Figure 1B:
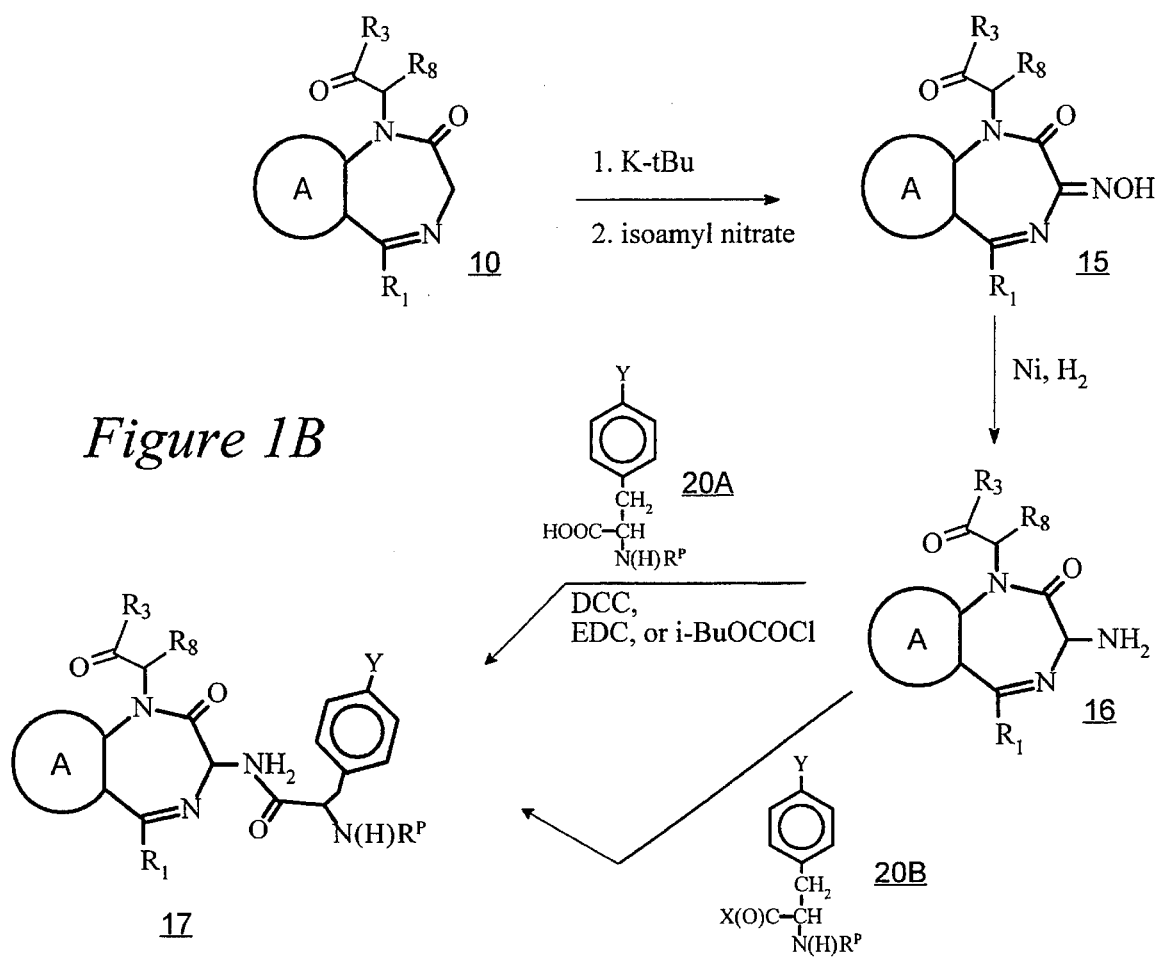
Figure 1C:
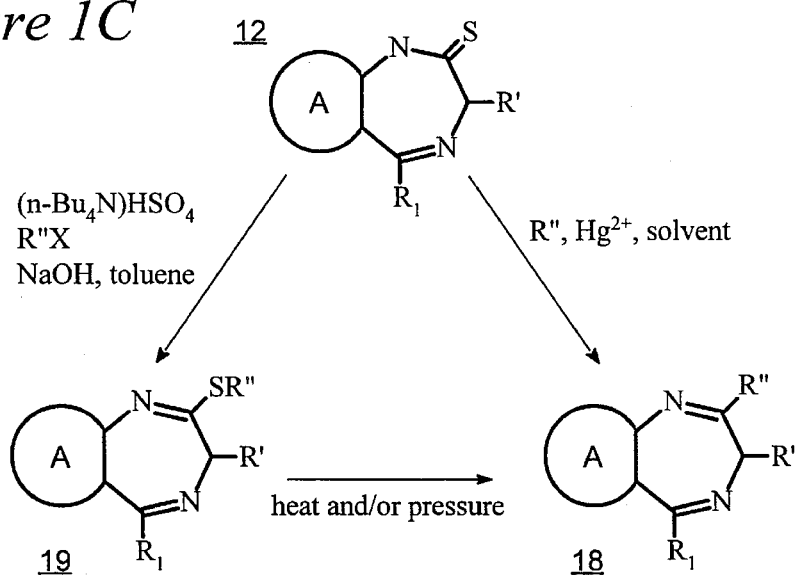

Further substitutions at $C_2$ can be carried out, for example, by treatment of the 2-thione 12 with an alcohol or an amine in solvent, preferably tetrahydrofuran, in the presence of a mercury salt, such as mercuric chloride or mercuric acetate, to produce the 2-substituted diazepine 18 (FIG. 1C). Alternatively, the 2-thione 12 can be converted to the thioiminoether 19 with an alkylating agent, preferably a lower alkyl halide or cycloalkyl halide, at room temperature under phase transfer conditions requiring aqueous base (such as an alkali earth hydroxide), an organic solvent immiscible with water (e.g. toluene), and a catalyst (e.g. tetra-n-butylammonium hydrogen sulfate). The thioiminoether 19 can, in turn, be transformed to the 2-substituted compound 18 by reaction with an amine or alcohol for 2–96 hours, such as in a sealed pressure vessel at 80°–250° C.

The 3-amino substituted diazepine 16 can be prepared by well known procedures. For example, FIG. 1B illustrates that the 3-unsubstituted diazepine 10 (R'=H) can be treated with a suitable base, such as potassium t-butoxide (K-tBu), followed by a nitrosylating agent, such as isoamyl nitrate, to yield the oxime 15. Reduction of the oxime, such as by treatment with Raney nickel, produces the 3-amino diazepine 16. Other exemplary methods for generating the 3-amino derivatives are described below with reference to FIGS. 2B and C, and FIG. 3. Referring further to FIG. 1B, the 3-amino substituted diazepine 16 can be derivatized with a phosphotyrosine or phosphotyrosine analog (collectively referred to hereinafter as "pTyr") to yield the 3-amide substituted compound 17. For example, the diazepine 16 can be alkylated by treatment with a pTyr halide 20B. Alternatively, the 3-amino 16 can be reacted with an N-protected phosphotyrosine 20A and a coupling reagent such as DCC, EDC, or isobutyl chloroformate.

Figure 2A:
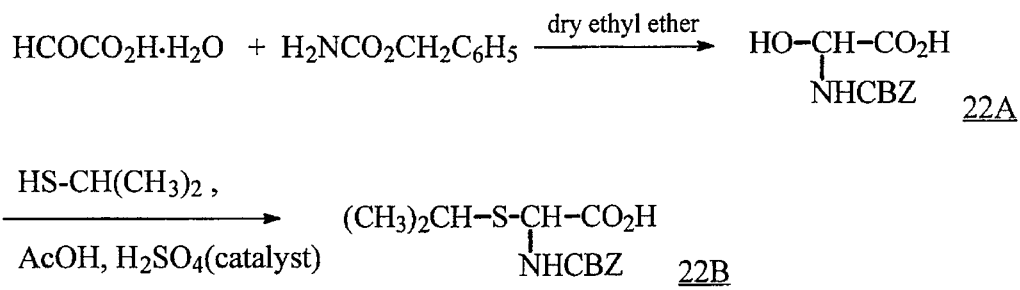
FIGS. 2A, 2B, 2C, and 2D depict a synthesis scheme for generating a benzodiazepine of the present invention by cyclization of an α-aminoglycine and a 2-amino benzophenone.
Figure 2B:
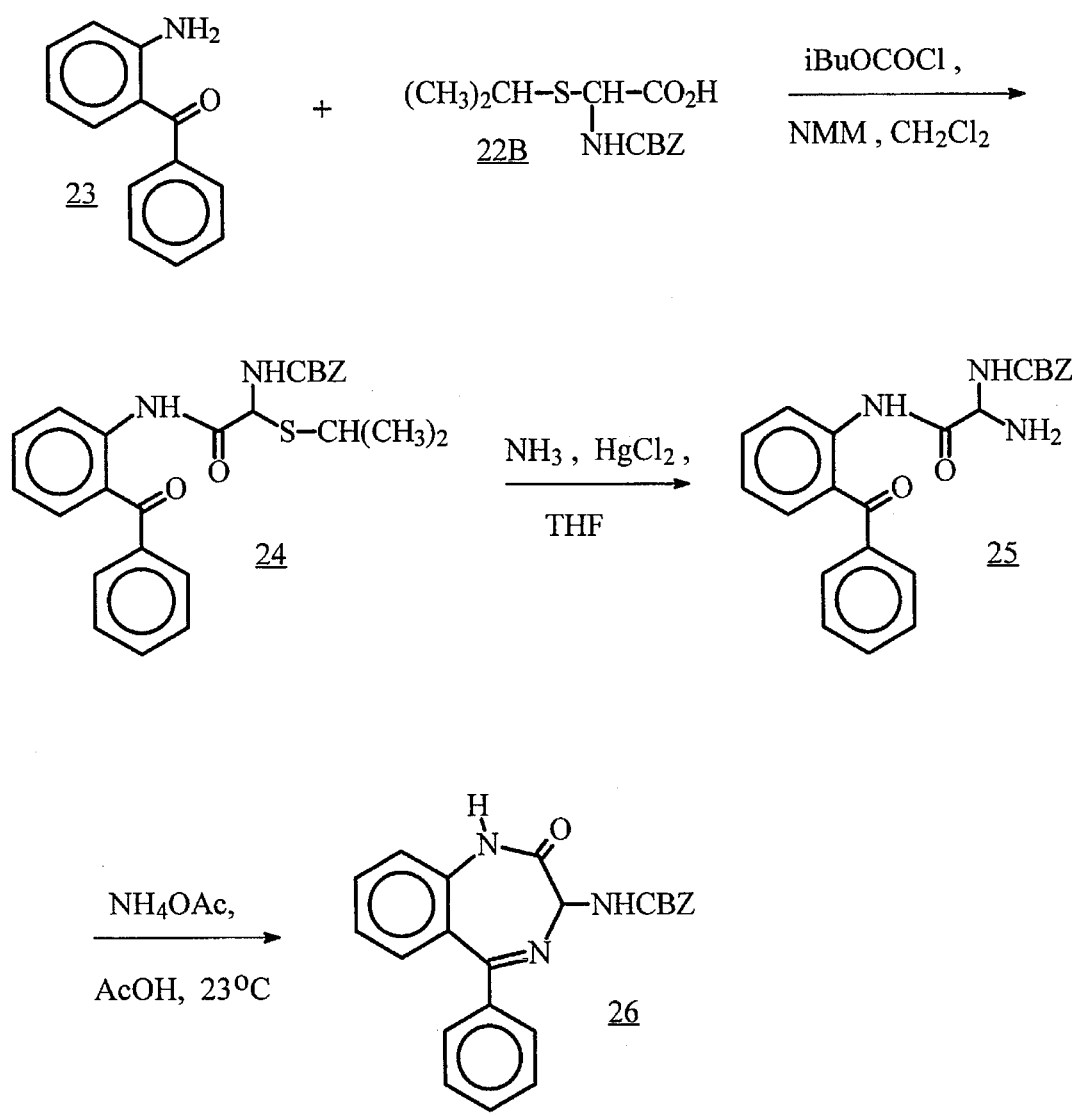

In an exemplary embodiment of the present invention, the synthesis of the subject peptidomimetic can be accomplished by the cyclization of an α-aminoglycine and a 2-amino benzophenone. As illustrated in FIG. 2A, the synthesis of α-isopropylthio-N-benzyloxy-carbonylglycine can be obtained in two steps from glyoxic acid, benzyl carbamate, and 2propanethiol according to the methods described by Zoller et al. (1975) *Tetrahedron* 31:863. Briefly, as described in the Examples below, a mixture of benzyl carbamate and glyoxylic acid is stirred in dry ether to yield α-hydrozy-N-benzyloxycarbonylglycine (22A). Addition of 2-propanethiol to a suspension of 22A in glacial acetic acid containing concentrated sulfuric acid as a catalyst yields the α-isopropylthio-N-benzyloxycarbonyl-glycine 22B.

The protected α-aminoglycine synthon 22B thus formed can be converted to the corresponding mixed anhydride with an alkyl chloroformate in the presence of a tertiary amine, and reacted in situ with a 2-aminocyclic ketone to yield a 1,4-diazepine. In accordance with the process illustrated in FIG. 2B, the aminoglycine 22B is dissolved in an aprotic solvent such as methylene chloride ($CH_2Cl_2$) and the resulting solution cooled to about 0° C. This solution is then mixed with an equimolar amount of N-methylmorpholine (NMM) and a similar amount of alky isobutyl chloroformate (iBuOCOCl), and the reaction mixture maitained at a temperature of 0° C. for approximately 15 minutes. To the resulting reaction mixture containing the mixed anhydride of 22B is then added dropwise an equimolar amount of the 2-aminobenzophenone 23. The reaction mixture is then allowed to warm to 25° C. and is stirred for about 18 hours at that temperature or heated up to about 55° C. for 2.5 hours to insure complete acylation reactions. This crude reaction mixture is then washed with aqueous citric acid, aqueous sodium bicarbonate solution and brine and after drying, the solvent removed by evaporation under reduced pressure, leaving the acylated product 24.

In accordance with the second step of the synthesis of the diazepine, the thioether substituent of 24 is first replaced with an amino group by treatment with excess ammonia in the presence of added mercury or silver salts to form intermediate 25. The solvent and salts are removed and the crude reaction product is cyclized in acetic acid containing ammonium acetate to produce the benzodiazepine 26. In a preferred embodiment, the thioether 24 is dissolved in tetrahydrofuran (THF) or other solvent inert under the reaction conditions and solution saturated with ammonia gas. A slight molar excess of mecuric chloride is added and a stream of ammonia gas passed into the reaction mixture for a period of 1–5 hours under ambient temperatures (e.g. 25° C.). The suspended solids and the solvent is then removed and the residual oily product is dissolved in excess acetic acid containing approximately 5 g ammonium acetate/100 ml acetic acid. The resulting solution is then protected from moisture and heated at 55° C. for 2.5 hours or stirred at 25° C. for 18 hours to produce the desired product, the N-protected 3-amino diazepine 26, which is recovered as a solid by evaporation under reduced pressure and partitioning the residual material containing the desired product between ethyl acetate and 1N sodium hydroxide solution.

Figure 2C:
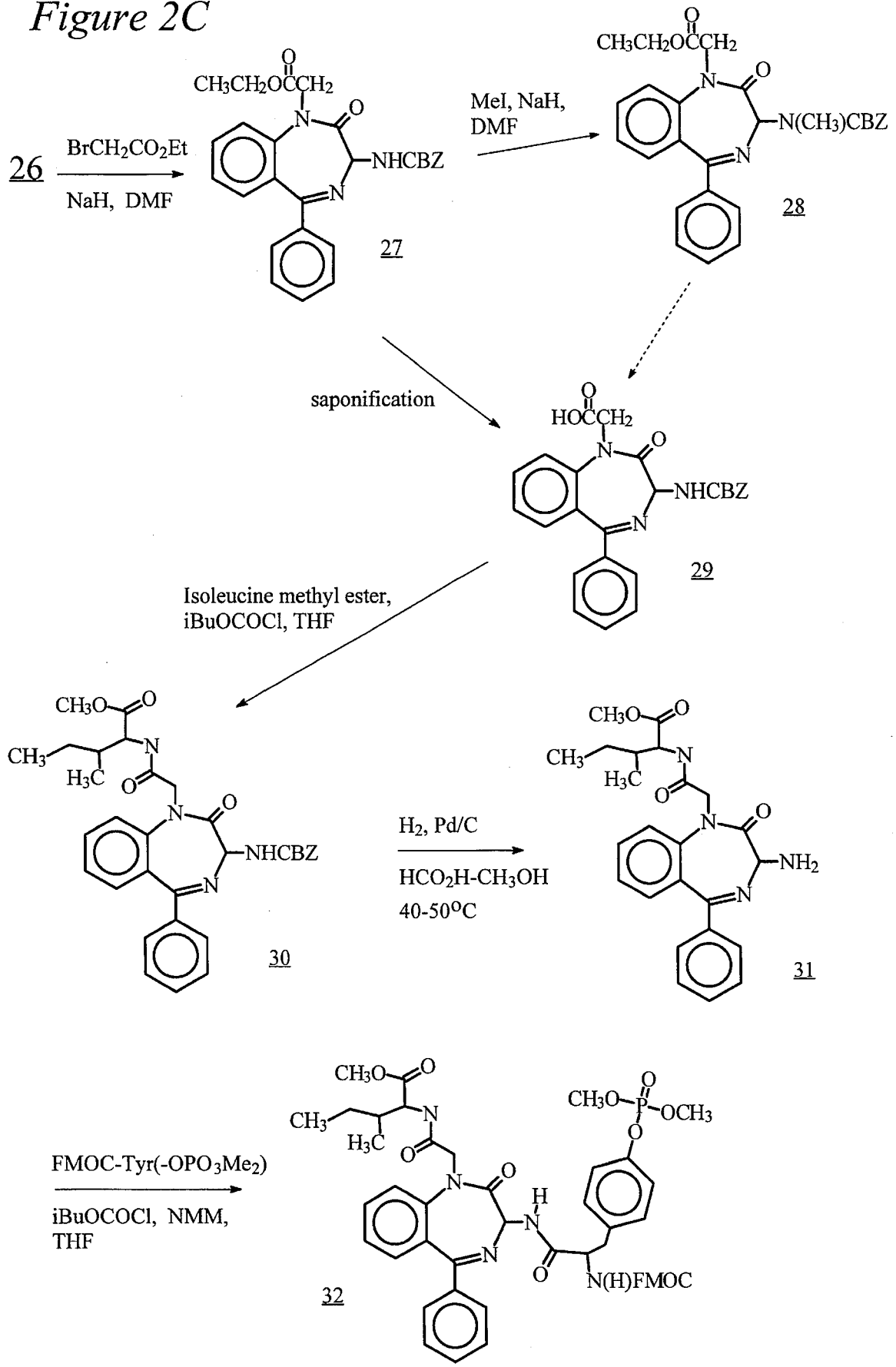

FIG. 2C depicts a preferred synthesis scheme for condensing amino acid residues with the diazepine core. 26 is alkylated at $N_1$ by treatment with sodium hydride and a halogenated alkyl ester, such as bromoethyl ethyl ester, in DMF, to form the 1-substituted ester 27. Subsequently, the ester can be saponified to yield the free carboxylic acid 29, which is then derivatized with an amino acid residue or peptide utilizing conventional peptide synthesis methods (see, for example, Barney and Merrifield, in *The Peptides*, E. Gross and J. Meienhofer, Eds. (Academic Press, New York, 1980), Vol. 2, pp. 1–284). For example, as depicted in FIG. 2C, the carboxyl intermediate 29 can be reacted with a c-protected isoleucine (e.g. isoleucine methyl ester) and a coupling reagent (isobutyl chloroformate) in NMM, to yield the 1-(2-isoleucinyl-2-oxoethyl)-diazepine 30.

In similar fashion, the diazepine 30 can be coupled with a phosphotyrosine analog, or a peptide having a carboxyl phosphotyrosine analog residue, utilizing standard peptide coupling protocols. For instance, the deprotection of the 3-amino moiety of 30 by removal of the benzyloxycarbonyl protecting group can be carried out under transfer hydrogenation conditions in methanol-aqueous formic acid to yield a formate salt of 30. The free amine 31 can be isolated after neutralization of the salt with sodium carbonate solution (10%) in ethyl acetate, and subsequently reacted with the N-protected (FMOC) phosphotyrosine analog in the presence of isobutyl chloroformate and N-methylmorpholine in tetrahydroturin, to yield the N-[2,3-dihydro-1-(2-methionyl-2-oxoethyl)-1,4-azepin-3-yl-2-one]-phosphotyrosine 32.

Removal of the FMOC protecting group, such as with HCl, provides the hydrochloride salts of the diasteromeric amide 32. The desired isomer can then be isolated, as for example, by crystalization.

Furthermore, FIG. 2C illustrates that the 3-amino moiety can be modified, such as by addition of a lower alkyl group (e.g. methyl). For example, the CBZ-protected amino moiety of the 27 can be methylated by treatment with sodium hydride and iodomethane in DMF to afford the 3-methyamine 28.

Figure 3:
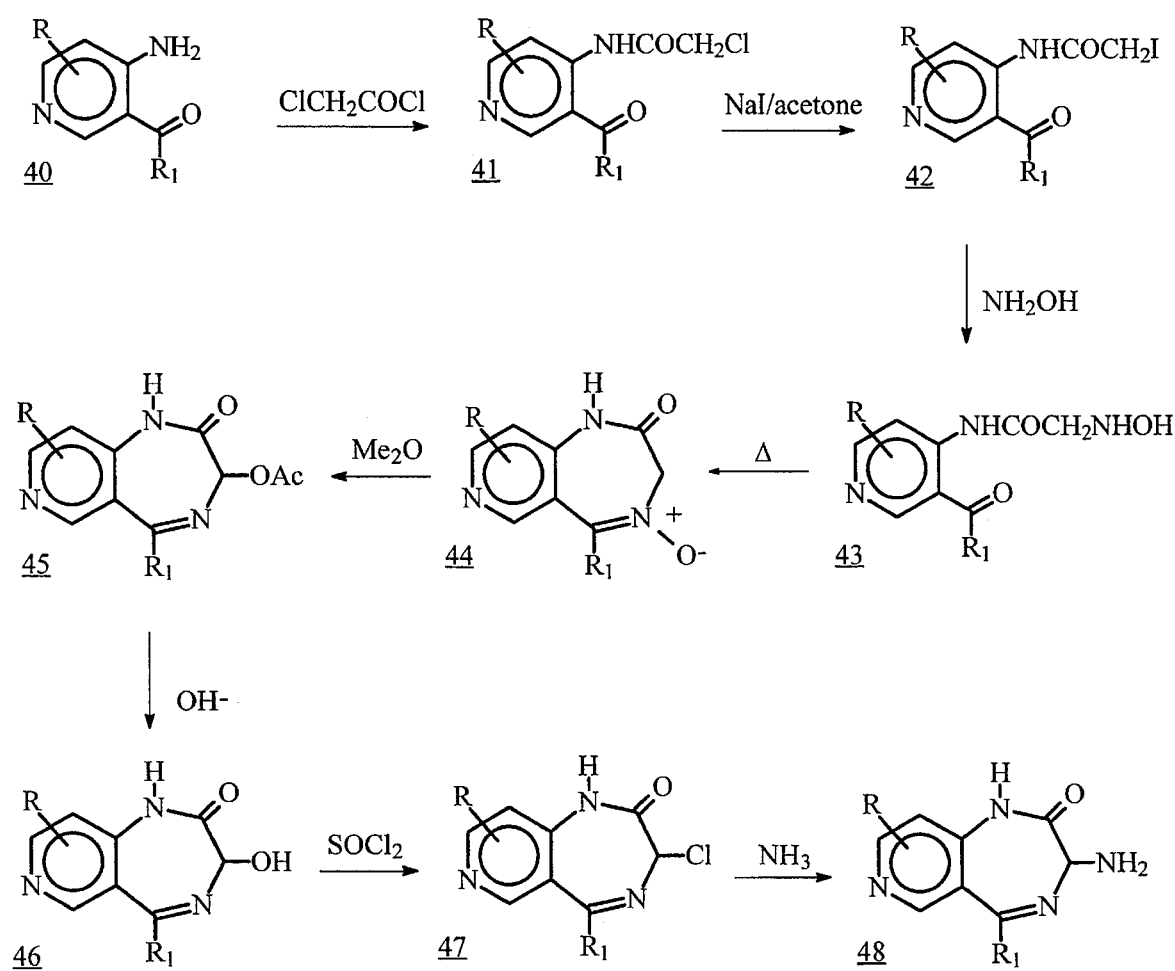
FIG. 3 shows yet another multistep synthetic approach useful in obtaining the present peptidomimetics, beginning with a 2-aminocyclic ketone.

In yet another embodiment, a synthetic approach useful in obtaining the present peptidomimetics comprises the multistep sequence shown in FIG. 3. This overall synthetic sequence is adequate for initial small-scale synthesis of a wide range of diazepines in order to investigate the inhibitory activity of a number of variants of a series of diazepine core structures in a high throughput screen as described below. Beginning with the 2-aminocyclic ketone 40, the iodoacetamide derivative 42 can be obtained by treatment with chloroacetyl chloride, followed by sodium iodide in acetone (Sternbach et al. (1962) *J. Org. Chem.* 27:3788). Treatment of 42 with ammonium hydroxide produces the intermediate 43, which can be cyclized by, for example, heating, to produce the diazepine core structure 44 (Bell et al. (1964) *J. Hetrocyl. Chem* 4:647; Hirai et al. (1980) *J. Med Chem.* 24:20; and Bock et al. U.S. Pat. No. 4,628,084). The 3-chloro-substituted diazepine 47 can subsequently be obtained from the 3-unsubstituted diazepine 44 by treatment with dimethyl ether, followed by base, followed by $SOCl_2$ (Bell et al. (1962) *J. Org. Chem.* 27:1691; and Bell U.S. Pat. No. 3,198,789). The resulting 3-chloro moiety can be displaced from the intermediate 47, as shown in FIG. 3, to form the 3-amino diazepine 48. Substitution of $N_1$ and the 3-amino moiety to form the subject peptidomimetics can be carried out as described above.

Figure 4:
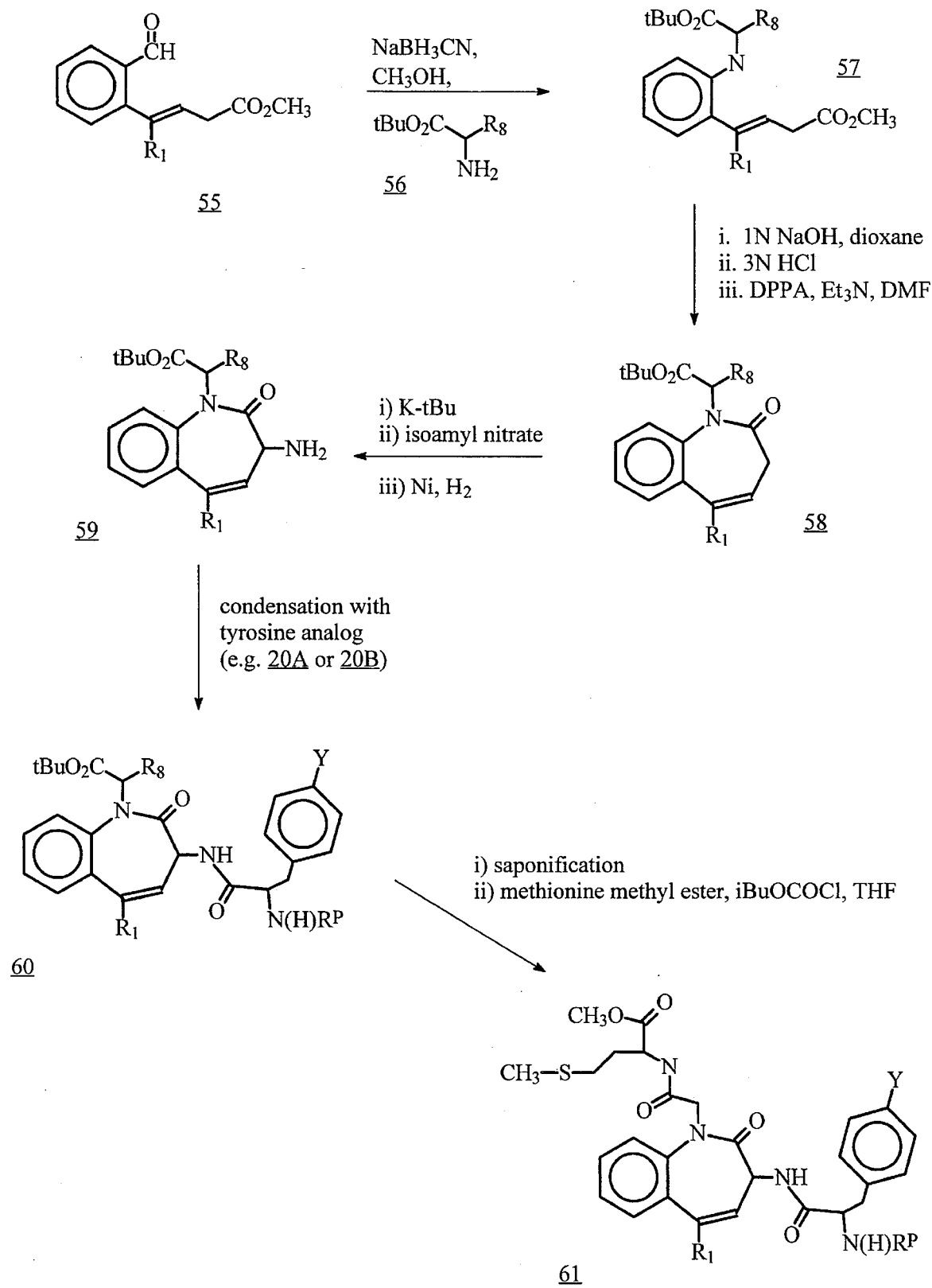
FIG. 4 illustrates a synthetic approach for generating the subject peptidomimetics comprising an azepine core having only one heteroatom by reductive amination and derivatization of an ortho-substituted aryl or heterocyclic ring with a carboxy-terminally protected amino acid analog, followed by cyclization to form the 1,5-disubstituted 1-azepine.

In yet another embodiment, the subject peptidomimetic comprises an azepine core having only one heteroatom (1-azepine; Formula II, Z=carbon atom). As FIG. 4 illustrates, the appropriate ortho-substituted aryl or heterocyclic ring 55 can be reductively aminated and derivatized with a carboxy-terminally protected amino acid analog 56, followed by cyclization to form the 1,5-disubstituted 1-azepine 58. The azepine ring, in similar fashion to the diazepine ring, can be converted to the 3-amino substituted form 59, which is subsequently used to generate the present peptidomimetics as described above. For example, the 3-amino azepine 59 can be reacted with an N-protected phosphotyrosine (or analog thereof) and a peptide coupling reagent such as DCC or EDC, to yield the 3-amino-PTyr azepine 60. Saponification of 60 followed by derizatiation with an amino acid residue utilizing, for example, methionine methyl ester and isobutyl chloroformate in THF, results in the N-[1-(2-methionyl-2-oxoethyl)-1-azepin-3-yl-2-one]-phosphotyrosine 61. The peptidomimetic 61 can be extended in either the carboxy or amino-terminal direction by standard peptide synthesis protocols. Alternatively, the C-terminal and/or N-terminal blocking groups can be removed or changed to a more suitable blocking group for the intended use or route of administration of the compound.

Figure 5A:
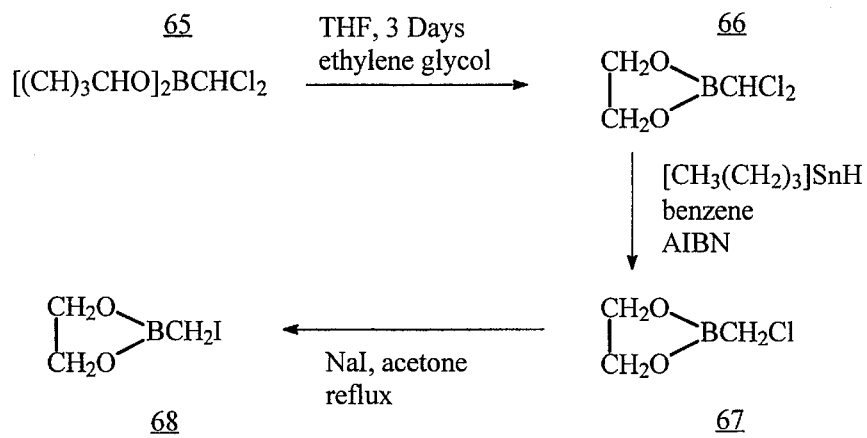
FIGS. 5A, 5B and 5C illustrate the synthesis of a 4-boronylphenylalanine which can be utilized to generate boronic acid analogs of phosphotyrosine.
Figure 5B:
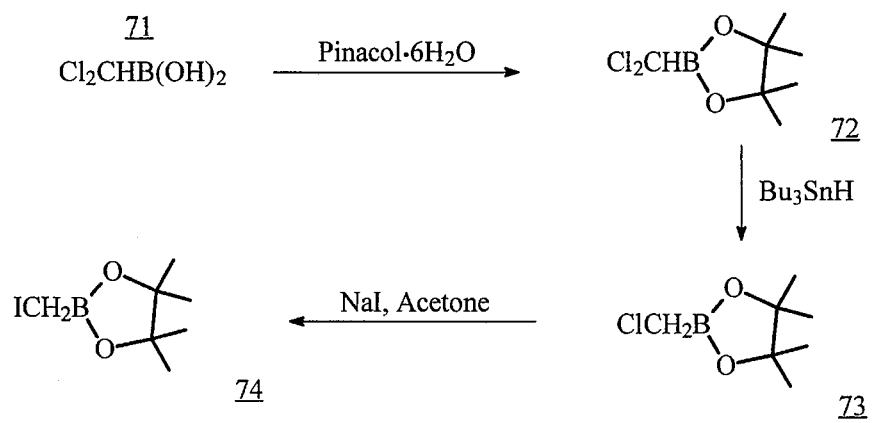
Figure 5C:
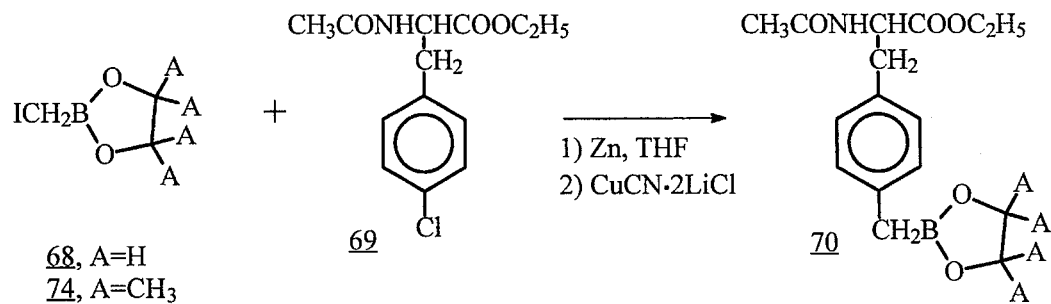

As described above, a number of phosphotyrosine analogs can be useful for generating the present peptidomimetics. In preferred embodiment, the phosphotyrosine analog is a non-hydrolyzable analog. For example, FIGS. 5A–C illustrate the synthesis of a 4-boronylphenylalanine which can be utilized to generate a boronic acid analog of phosphotyrosine. Briefly, ethylene glycol is added to diisopropyl dichloromethaneboronate 65 dissolved in THF, stored for 3 days at room temperature, and subsequently fractionally distilled to yield the 2-dichloromethyl-2-bora-1,3-dioxacyclopentane 66. Tri-n-butyltin hydride is added to a solution of 66 in dry benzene. A catalytic amount of 2,2'-azobis-(2-methylpropionitrile) is introduced and the resulting solution is stirred for 24 hours at room temperature. Fractional distillation of the resulting solution yields the 2-chloromethyl-2-bora-1,3-dioxacyclopentane 67, which can be converted to the 2-iodomethyl compound 68 by addition of sodium iodide to a solution of 67 in dry acetone and refluxing for 48 hours. (Wutz et al. (1982) *J. Organometal. Chem.* 234:137–141).

FIG. 5B illustrates another embodiment of an activated boronate tier synthesizing a boronic acid analog of tyrosine. As depicted, dichloromethaneboronic acid 71 (Rathke et al. (1976) *J. Organometal Chem.* 122:145) is dissolved in benzene along with pinacol $6H_2O$. The resulting biphasic mixture is then heated to reflux under an argon atmosphere, utilizing a Dean-Spark trap to remove water as a azeotrope. After 72 hours at reflux, the resulting solution is fractionally distilled to yield the 4,4,5,5-tetramethyl-2-dichloromethyl-2-bora-1,3-cyclopentane 72. Following the procedure illustrated in FIG. 5A for the preparation of the 2-chloromethyl 67 from the 2-dichloromethyl 66, the 2-chloromethyl 73 can be generated, and, in similar fashion as described above, can be subsequently converted to the 4,4,5,5-tetramethyl-2-iodomethyl-2-bora-1,3-cyclopentane 74 for use in synthesizing a boronate pinacol analog of phosphotyrosine.

FIG. 5C illustrates a general preparation scheme for condensing boronyl esters such as 68 and 75 with a halogen-activated phenylalanine, such as 4-chlorophenylalanine 69. Following the procedures of Knochel (1990) *J Amer Chem Soc* 112:7431–7433, a typical reaction scheme would comprise first activating zinc dust with dibromomethane (under an argon atmosphere), followed by dropwise addition of a THF solution containing the boronyl ester while stirring at 25° C. for approximately 0.5 to 2 hours. The zinc dust is then decanted and transferred to a solution made of copper cyanide, lithium chloride, and THF. The resulting copper derivatives are then reacted with the acyl halide 69 to generate the boronate 70, which can be utilized in the synthesis of the subject peptidomimetics.

The peptidomimetics of the present invention, such as libraries of variants of formula I having various representative classes of substituents, can be rapidly screened in high throughput assays in order to identify potential lead compounds for inhibiting the ability of a particular SH2 domain to bind a phosphotyrosine-containing polypeptide. For instance, the basic strategy of the "two-hybrid" assay (Fields et al. (1989) *Nature* 340:245–246) can be employed to rapidly screen the compounds of the present invention. In this assay system, the N-terminal domain of GAL4 (or other similar protein), which binds to specfic DNA sequences (UASG), is used to generate a fusion protein (GAL4-DB/SH2) with at least an SH2-domain containing portion of a protein. The C-terminal domain of GAL4, which is necessary to activate transcription by GAL4, is used to create a fusion protein (GAL4-AD/target) with a phosphotyrosine-containing polypeptide target of the SH2 domain of interest. Thus, under circumstances wherein the SH2 domain is capable of binding the phosphotyrosine of the target protein, the resulting fusion protein complex will reconstitute proximity of the GAL4 domains, and transcription of a gene regulated by $UAS_G$ can occur. To further illustrate, the $UAS_G$ sequence can be utilized to generate a reporter gene construct, such as a luciferase gene construct, which is then used to transfect host cells. Expression of the reporter gene thus requires the presence of the reconstituted GAL4 domains.

In another aspect, the present invention provides pharmaceutically acceptable compositions which comprise a therapeutically-effective amount of one or more of the compounds of Formula I, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The phrase "therapeutically-effective amount" as used herein means that amount of a compound, material, or composition comprising a peptidomimetic of Formula I which is effective for producing some desired therapeutic effect through inhibiting an intracellular signalling pathway in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present SH2-inhibitors may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of peptidomimetics of the present invention. These salts can be prepared in situ during the final isolation and purification of the peptidomimetics of the invention, or by separately reacting a purified peptidomimetic of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

In other cases, the peptidomimetics of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of peptidomimetics of the present invention. These salts can likewise be prepared in situ during the final isolation and purification of the peptidomimetics, or by separately reacting the purified peptidomimetic in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BIA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (peptidomimetic of Formula I) which can be combined with a carrier material to produce a single dosage form will vary depending upon the host being treated, the particular mode of administration. The amount of active ingredient which can be combined with a carrier material to produce a single dosage form will generally be that amount of the peptidomimetic which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a peptidomimetic of the present invention with the carrier and, optionally, one or more accessory ingredients. In general, the formulations are prepared by uniformly and intimately bringing into association a peptidomimetic of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a peptidomimetic of the present invention as an active ingredient. A peptidomimetic of the present invention may also be administered as a bolus, electuary or paste.

In solid dosage forms of the invention for oral administration (capsules, tablets, pills, dragees, powders, granules and the like), the active ingredient (peptidomimetic of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptidomimetic moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the peptidomimetics of the invention include pharmaceutically acceptable emulsions, microemulsions, solutions, suspensions, syrups and elixirs. In addition to the active ingredient (peptidomimetic of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active peptidomimetics, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more peptidomimetics of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active peptidomimetic.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a peptidomimetic of this invention include powders, sprays, ointments, pastes, creams, lotions, gels, solutions, patches and inhalants. The active peptidomimetic may be mixed under sterile conditions with a pharmaceutically-acceptable carrier, and with any preservatives, buffers, or propellants which may be required.

The ointments, pastes, creams and gels may contain, in addition to an active peptidomimetic of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a peptidomimetic of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a peptidomimetic of the present invention to the body. Such dosage forms can be made by dissolving or dispersing the peptidomimetic in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Opthalmic formulations, eye ointments, powders, solutions and the like, are also contemplated as being within the scope of this invention.

Pharmaceutical compositions of this invention suitable for parenteral administration comprise one or more peptidomimetics of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject peptidomimetic in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the peptidomimetics of the present invention are administered as pharmaceuticals, to humans and animals, they can be given per se or as a pharmaceutical composition containing, for example. 0.1 to 99.5% (more preferably, 0.5 to 90%) of active ingredient in combination with a pharmaceutically acceptable carrier.

The peptidomimetics of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subaraclmoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

In yet a further aspect, the present invention provides a method for eliminating or ameliorating pain in an animal comprising administering a therapeutically-effective amount of a peptidomimetic of Formula I, as described hereinabove, to the animal.

These peptidomimetics may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the peptidomimetics of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular peptidomimetic of the present invention employed, or the ester, salt or amide thereof, the route of administration, the time of administration, the rate of excretion of the particular peptidomimetic being employed, the severity of the pain, the duration of the treatment, other drugs, compounds and/or materials used in combination with the particular peptidomimetic employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the peptidomimetic of the invention employed in the pharmaceutical composition at levels lower than that required in order to achieve the desired therapeutic effect and gradually increase the dosage until the desired effect is achieved.

In general, a suitable daily dose of a peptidomimetic of the invention will be that amount of the peptidomimetic which is the lowest dose effective to produce a therapeutic effect. Such an effective dose will generally depend upon the factors described above. Generally, intravenous, intracerebroventricular and subcutaneous doses of the peptidomimetics of this invention for a patient, when used for the indicated analgesic effects, will range from about 0.0001 to about 100 mg per kilogram of body weight per day.

If desired, the effective daily dose of the active peptidomimetic may be administered as two, three, four, five, six or more sub-doses administered separately at appropriate intervals throughout the day, optionally, in unit dosage forms.

While it is possible for a peptidomimetic of the present invention to be administered alone, it is preferable to administer the peptidomimetic as a pharmaceutical formulation (composition).

It is yet another aspect of the present invention to utilize the subject peptidomimetics to modulate intracellular signaling pathways by disrupting particular protein-protein interactions mediated by SH2 domains. For instance, the subject peptidomimetics can be contacted with a cell, either in vivo (e.g. administered to a patient or animal) or in vitro (e.g. employed in cell culture), to affect the responsiveness of a cell to a growth factor, cytokine or other receptor ligand; as an immunosuppressant; to prevent osteoclastic resorption of bone during osteoporosis; influence differentiation of cells; to modulate cellular response to interactions with the extracellular matrix, as well as affect the production and secretion of extracellular matrix components; prevent viral infection and/or viral-mediated transformation of cells; and to inhibit the proliferation of transformed cells or to render transformed cells more sensitive to cytostatic or cytotoxic agents. The SH2 target of the subject inhibitors can range from the interaction between, for example, an activated receptor complex and the initial cytoplasmic proteins involved in triggering a particular set of intracellular signaling pathways, to the last SH2-mediated interaction in a specific pathway, such as the formation of a transcription factor complex or allosteric regulation of an enzymatic activity. Thus, the inhibitors of the present invention can be used to prevent the interaction between a phosphotyrosine residue and such SH2-containing signal transduction proteins as, for example, Src, Lck, Fps, phosphatidylinositol-3-kinases, ras GTPase-activating protein, Fyn, Lyk, Fgr, Fes, ZAP-70, Abl, Crk, Nck, Sem-5, p85, phospholipase C, SHPTP1, SHPTP2, corkscrew, Syk, Lyn, Yes, Hck, Dsrc, Tec, Atk/Bpk, Itk/Tsk, Arg, Csk, tensin, Vav, Shc, Emt, Grb2, Syp, Blk, Bpk 113TF, 91TF, and Janus kinases including Tyk2, JAK1 and JAK2. It is understood in the art that the above designations may in some instances refer to a family of related proteins which may include tissue-type specific expression, arising from, for example, differential splicing. Moreover, in light of the present invention, one skilled in the art will be able to easily ascertain other SH2 proteins whose phosphotyrosine binding abilities can be inhibited with the subject compounds.

Binding of growth factors, differentiation factors, cytokines and other receptor ligands to cell surface receptors, as well as interaction of the cell with extracellular matrix components, and even fluxuation of intracellular ion concentrations (particularly calcium), are frequently causative agents in the induction of signal transduction pathways which activate protein tyrosine kinases and result in modulation of gene expression and cell morphology. For instance, a number of mechanistically distinct signal pathways, mediated by tyrosine phosphorylation states and linking cell surface receptors to transcriptional factors and other enzymes, are understood to exist.

In one aspect of the invention, the subject peptidomimetic inhibits the signal transducing ability of an SH2 protein having an enzymatic activity. Exemplary enzymes include cytoplasmic tyrosine kinases (e.g. src, abl, lck, nck), phosphotyrosine phosphatases, phospholipase C$\gamma$ (PLC$\gamma$), ras GTPase activating proteins (rasGAPs), and nucleotide echange factors (Koch et al. (1991) *Science* 252:668–674). Thus, preventing SH2-mediated interactions with the compounds of the present invention can inhibit the compartilization or localization of an SH2-containing enzyme by disrupting a phosphotyrosine-SH2 mediated interaction which would otherwise act to sequester the enzyme at a particular cellular location, such as at the cytoplasmic face of the cell membrane. Alternatively, the subjet inhibitors can be used to modulate the regulation of SH2-containing enzymes by inhibiting the formation of specific multiprotein complexes, or other forms of allosteric control. Illustrative of therapeutic targets of this class of SH2 protein include a number of inducers of signal transduction pathways, such as growth factors like EGF, PDGF, nerve growth factor (NGF) or insulin, are generally understood to activate one or more tyrosine kinase cascades, which include members of the src-family of protein tyrosine kinases, that eventually lead to activation of transcriptional factors localized in the nucleus. Likewise, several tyrosine kinases of the src-family are coupled to cell surface receptors in lymphocytes and function as signal transducers after specific ligand binding. Examples are the associations of CD4 and CD8 with lck (Veillette et al. (1988) *Cell* 55:301–308), interleukin-2 receptor $\beta$ chain with lck (Hatakeyama et al. (1991) *Science* 252:1523–1528), T cell receptor complex with fyn (Samelson et al. (1990) PNAS 87:4358–4362), and the immunoglobulin receptor complex with lck, lyn, fyn, and blk (Yamanashi et al. (1991) *Cell Regul.* 2:479–987; and Burkhardt et al. (1991) PNAS 88:7410–7414). These interactions implicate src-related kinases in the regulation of a variety of intracellular events, from lymphokine production and cytotoxicity, to the expression of specific nuclear binding proteins. Such receptor-src interactions represent a first step in a cascade of intracellular events. For instance, a proximal and critical biochemical event upon T cell antigen receptor (TCR) stimulation is the activation of a protein tyrosine kinase pathway. ZAP-70, a PTK of the p72syk family, associates with phosphorylated TCR subunits through its SH2 domains, and has a remarkably restricted repertoire of protein binding (Wange et al. (1993) *J Biol Chem* 268:19797–19801). Alternatively, some cytoplasmic tyrosine kinases may serve essential regulatory functions. For example, csk is beleived to modify the activity of other tyrosine kinases (i.e. src subfamily) and down regulate the signal transduction pathways in which they participate (Nada et al. (1991) *Nature* 351:69–72; Okada et al. (1991) *J Biol Chem* 266:24249–24252).

Other signal transduction pathways involve the regulation of non-PTK enzymes by controlling subunit compositions or through other forms of allosteric control, and represent potential targets for inhibition by the subject compounds. Such allosteric regulation of the oncoprotein ras, which forms part of a signal cascade that links tyrosine kinase-associated receptors to nuclear events involved in mitogenesis, represent an inhibitory target for the subject peptidomimetics. Ras proteins and their relatives play critical roles in the control of normal and transformed cell growth, regulating many aspects of growth and differentiation, control of the cytoskeleton and traffic between various membrane-bound compartments in the cell. For instance, interleukin-3, erythropoietin, and steel factor all induce the tyrosine phosphorylation of the SH2-containing protein, p52shc. The formation of a complex between p52shc and the adaptor protein, Grb2, is an apparent direct link of tyrosine phoshphorylayion events to the activation of ras in hemopoietic progenitors and believed to be a critical step in stimulating these cells to transit through G1 to S phase and enter into mitosis (Cutler et al. (1993) *J. Biol Chem* 268:21463–21465).

Still other signaling pathways involve activation of cytoplasmic transcriptional factors by tyrosine phosphorylation, which can be disrupted at several different levels through the use of the present compounds. For example, in a "direct effector" system, transcriptional factors with SH2 domains bind directly to ligand-activated, receptor-associated tyrosine kinase(s). This association of the kinase and transcriptional factors in turn results in tyrosine phosphorylation and activation of the transcriptional factor, triggering its localization to the nucleus and mediating formation of an active transcriptional complex with other nuclear DNA-binding proteins. To illustrate, it has been shown that subunits of the interferon-α induced transcription factor complex ISGF3 (namely, the transcriptional factor subunits 113TF, 91TF, and 84TF) contain SH2 domains and are directly activated by tyrosine phosphorylation in the cytoplasm. These activated subunits translocate to the nucleus to form an active transcriptional complex with p48. A variety of other growth factors and cytokines, including interferon-T, EGF, PDGF, CSF-1, IL-3, IL-5, IL-10, CNTF, LIF and GM-CSF, employ a pathway similar to that of interferon-α, in that are capable of activating transcriptional factors having SH2 domains (Fuet al. (1992) *Cell* 70:323; Montminey (1993) *Science* 261:1694; Larnet et al. (1993) *Science* 261:1730; Ruff-Jamison et al. (1993) *Science* 261:1733; Silvennoinen et al. (1993) *Science* 261:1736; Sadowski et al. (1993) *Science* 261: 1739; and Shuai et al. (1993) *Science* 261: 1744). Disruption of transcriptional regulation mediated by such factors can be accomplished with the subject peptidomimetics by inhibiting the interaction of the transcription factor with an upstream activating kinase, or by inhibiting the interaction of the phosphorylated transcription factor with other SH2-containing transcription factors to form active complexes.

As indicated above, frequent among the components of each of these signal transduction pathways are proteins that contain one or more SH2 domains. For example, interactions between phosphotyrosine residues on autophosphorylated receptors and SH2 domains of signal-transducing proteins are critical for the formation of signal transduction complexes, and represent the initial transduction signals which stimulate a cascade of additional molecular interactions involved in disseminating the signal throughout the cell by complex, branching pathways that coordinate multifunctional cellular programs and control cell behavior. Each of the receptor binding proteins control at least one cellular pathway involved in the biological response to the growth factor. By targeting particular SH2-mediated interactions with the subject peptidomimetics, selective intracellular signaling pathway targets can be inhibited so as to grossly alter the cell's response parameters to the external stimulus at one extreme, or, at the other, to result only in modification of particular portion(s) of the cell's physiological response to the stimulus.

In an illustrative embodiment, the subject peptidomimetics are utilized to modulate the response of a cell to a growth factor or cytokine. It is generally understood that the binding of growth factors to their membrane receptors activates a cascade of intracellular signaling pathways that regulate phospholipid metabolism, arachidonate metabolism, protein phosphorylation, calcium mobilization and transport, and transcriptional regulation. These signaling events can result in a diversity of changes in transport properties, acute metabolic activities, membrane trafficking, cytoskeletal interactions, and the programming of gene induction governing cell growth, differentiation, and migration. Abberations in these growth factor-induced events are, for example, associated with a variety of hyperproliferative disorders such as leukemia, cancer, psoriasis, atherosclerosis, and restinosis.

A variety of polypeptide growth factor receptors have been characterized, some which possess intrinsic protein tyrosine kinase activity such as the receptors for epidermal growth factor (EGF), platelet-derived growth factor (PDGF), insulin, and certain protooncogene products including c-kit (the stem cell factor receptor) and c-fms (the macrophage colony-stimulating factor receptor); others of which have no intrinsic kinase acitivity but which sequester tyrosine kinases from the cytosol upon ligand binding, such as the receptors for interleukin-6, ciliary neurotrophic factor (CNTF), and Oncostatin-M. Each of these classes of receptor contain distinct binding sites that serve to recruit multiple signaling molecules through protein-protein interactions, and can activate both overlapping and distinct sets of genes and effectuate a wide range of biological responses in target cells.

In an exemplary embodiment, the subject peptidomimetics can be used to inhibit proliferation of transformed cells that are stimulated by autocrine feedback loops. For example, a variety of human tumors frequently express high levels of both EGF receptors and one of its ligands, transforming growth factor alpha (TGFα). The synthesis and release of TGFα by a cell also able to be stimulated by this ligand is widely believed to create stimulatory autocrine loops (Baselga et al. (1993) *J Natl Cancer Inst* 85:1327–1333; and Fan et al. (1993) *Cancer Res* 53:4322–4328). Moreover, it has become apparent that 20 to 30 percent of cancer disease is characterized by transformed cells expressing oncogenic products which are growth factor receptors or their mutated homologs, and which exhibit protein tyrosine kinase activity. That is, they are capable of constitutive activation of signal transduction processes which drive the cell's proliferation. Inhibition of one or more intracellular signaling pathways by the present compounds can inhibit proliferation of tumor cells, and may be used alone or for potentiating the efficacy of other chemotherapeutic agents. To illustrate, the cell can be contacted with one or more peptidomimetics of the present invention suitable for inhibiting the interaction of the activated EGF receptor with such SH2-containing proteins as phospholipase C-γ, Grb2, syp, the p85 subunit of phosphotidylinositol-3-kinase, abl, nck, the transcription factor p91, or a combination thereof, so as to prevent signal transduction events which are involved in mitogenesis and cell proliferation. In another embodiment, the subject compounds can be utilized to inhibit SH2-mediated interactions of the chimeric oncoprotein BCR-ABL (with, for example, grb2), which has been implicated in the pathogenesis of Philadelphia chromosome-positive human leukemias.

The subject peptidomimetics can also be used to modify only a portion of the biological response of a cell to a particular growth factor. For instance, sensitivity of a particular cell to a growth factor, or other mitogenic stimulus, which utilizes a ras signalling pathway can be either up-regulated or down-regulated by disruption of the SH2-mediated interactions of the ras protein and effector proteins which allosterically control the GTPase activity. As noted above, many tyrosine kinases, including the receptors for hormones. such as EGF, NGF and insulin, transmit intracellular signals through Ras proteins. Ligand binding to such receptors stimulates ras guaninine-nucleotide exchange activity and increases the level of GTP-bound ras, suggesting that these tyrosine kinases may activate guanine-nucleotide exchange factors (rasGEFs). Grb2, which binds the autophosphorylated EGF receptor through its SH2 domain, links the EGF receptor to a rasGEF. Thus, the effect of inhibiting the ability of a rasGEF to interact with, and activate a ras-type protein can be used to desensitize a cell to a particular stimulus. Conversely, targeting the subject inhibitors to the interaction between a ras protein and an inactivating subunit, such as a GTPase-activating protein (rasGAP), can be used to increase the sensitivity of the cell to a stimulus by prolonging the half-life of activated ras proteins (e.g. GTP-bound forms). In similar fashion, the present peptide analogs can be used to exploit the often antagositic relationships between a kinase and a phosphatase in signal transduction, by regulating the activity and/or localization of one of two. In one embodiment, the subject inhibitors can be used to increase the sensitivity of a cell to a cytokine or growth factor which is pyrogenic in an animal (e.g. CNTF, IL-6 or LIF). Thus, lower doses of the factor can be used and unwanted side effects can be minimized.

In yet another embodiment, the subject peptidomimetics can be used to modulate an immune response, such as to cause general or specific immunosuppression. For instance, the compounds of the present invention can be used to prevent antigen-specific or mitogen-induced differentiation and proliferation of B lymphocytes. As noted above, engagement of the B-cell antigen receptor complex induces immediate activation of receptor-associated Src family tyrosine kinases including p55blk, p59fyn, p53/561yn, and perhaps p561ck. These kinases act directly or indirectly to phosphorylate and/or activate effector proteins including the microtubule-associated protein kinase (MAPK), phospholipase C-γ1 (PLC-γ1),I) and C-γ2 (PLC-γ2), phosphatidylinositol-3-kinase (PI-3-K), and p21ras-GTPase-activating protein (GAP). Receptor ligation triggers the activation of multiple receptor-associated src-family kinases leading to phosphorylation and activation of PLC-γ1 and PLC-γ2. Subsequent phosphoinositide hydrolysis and calcium mobilization, presumably acting in concert with other tyrosine kinase-activated mechanisms, leads to transcriptional activation of a number of immediate early genes and, ultimately, to B cell proliferation. Targetting such signal transduction pathways can result in inhibition of B-cell activation.

Likewise, another aspect of the present invention comprises the inhibition of T cell activation. Signal transduction through the T-cell receptor and cytokine receptors on the surface of T lymphocytes occurs largely via tyrosine phosphorylation of intracellular substrates. Several members of the src and syk families of tyrosine kinases have been implicated in signal transduction in lymphocytes, as well as other unique tyrosine kinases, such as emt, that are expressed mainly in T lymphocyte. Inhibition of certain signal pathways mediated by SH2 proteins can therefore be used to suppress activation of T cells.

It is also worth noting that emt appears related to the B-cell progenitor kinase (bpk), which has been implicated in X-linked hypogammaglobulinemia, to the tecI mammalian kinase, which has been implicated in liver neoplasia, and to the more widely expressed tecII mammalian kinase (Gibson et al. (1993) *Blood* 82:1561–1572), each of which represent potential therapeutic targets for compounds of the present invention.

While the above mechanism of inhibition resembles the induction of clonal anergy, it is also possible to utilize the subject compound to induce clonal deletion. It is generally understood that proliferation of T lymphocytes is triggered by the interaction of IL-2 with its specific receptor following T lymphocyte activation. Activation of T cells is also associated with an upregulation of IL-2 receptors (IL-2R) on the induced cells. The receptor for IL-2 consists of at least three distinct subunits, the beta chain of which is understood to be critical for receptor-mediated signalling through physical association with, and activation of, a src-family protein kinase (p561ck). It is now evident that IL-2R beta is linked to at least two intracellular signalling pathways that mediate nuclear proto-oncogene induction. One pathway is linked to the induction of the c-los, c-jun, and other genes of this family. Another pathway leads to c-myc gene induction. By specifically inhibiting the pathway leading to fos and jun expression, but not inhibiting IL-2 induction of myc, the subject peptidomimetics can be used to cause apoptosis of activated T cells, thereby deleting those clones activated in response to a particular antigenic stimulus. Such protocols can be used, for example, in conjunction with organ and tissue transplantation, to prevent, for example, rejection of the graft by the host, or graft-versus-host disease mediated by T lymphocytes of the graft. The same strategy can also be carried out to induce clonal deletion of B-lymphocytes.

This being the case, the present compounds may also be used to modulate expression of the early-intermediate genes (cIE), such as fos, jun, and myc, in other tissue in order to prevent apoptosis. For example, the compounds of the present invention can be used to prevent apoptotic events in neurodegenerative disorders associated with activation of cIE genes by, for example, calcium-induced intracellular signalling or excititory amino acids.

In yet another embodiment of the present invention, the subject compounds can be used to inhibit certain biological actions of such mitogens as vascular endothelial growth factor (VEGF). For instance, the subject peptidomimetics can be employed to inhibit the abnormal proliferation of smooth muscle which takes place in atherosclerosis and which is induced by VEGF. Likewise, another aspect of the present invention comprises inhibiting the angiogenic acitivity of VEGF in order to prevent vascularization of hyperproliferative tissue, particularly in the treatment of endometriosis.

In another embodiment, the subject inhibitors can be used to affect the differentiation of a cell or tissue. For instance, EGF plays an important physiological role in the control of adipocyte differentiation, as a potent inhibitor of adipose differentiation and inhibitor of adipose tissue development. (Serrano et al. (1993) *Am J Physiol* 264:E800–803). Thus, depending on whether the effects of EGF are enhanced or diminished by the choice of SH2 inhibitor, the present compounds can be used in livestock to repartition nutrients between subcutaneous fat and other carcass components, including muscle, skin, bone and certain organs.

In still a further embodiment of the present invention, the subject peptidomimetics can be used to control the response of cells to extracellular matric interactions. For example, the present compounds can be employed to modulate the biological consequence of integrin-mediated cell adhesion to extracellular matrix components. It is generally understood that occupation of integrins can result in the transduction of intracellular signals, leading to cytoskeletal reorganization and induction of gene expression. Such physiological events are believed to mediated, at least in part, by potential targets for the subject compounds, such as the observed accumulation of p21ras in the active GTP bound state (Kepron et al. (1993) *J Biol Chem* 268:20701–20704) or phosphotyrosine accumulation. Indeed, the treatment of cells with the tyrosine kinase inhibitor herbimycin A diminishes the adhesion-induced tyrosine phosphorylation of intracellular proteins, and inhibits the formation of focal adhesion and stress fibers (Burridge et al. (1992) *J Cell Biol* 119:893–903).

In one aspect, the subject inhibitors are useful for disrupting the signal transduction pathway(s) originating from the leukocyte response intregrin (LRI), which mediate adhesion, chemotaxis, and activation of increased phagocytic potential by neutrophils (PMN) and monocytes (Carreno et al. (1993) *Clin Immunol Immunopathol* 69:43–51).

Another aspect of the present invention comprises inducing chondrogenesis by affecting the integrin-mediated differentiation of chondrocytes which ordinarily inhibits cartilage synthesis. The modulation of the chondrocyte phenotype, between mature fibrochonrocytes and cartilage-producing chondroblasts, is related to integrin-mediated intracellular signalling (Loeser et al. (1993) *Arthritis Rheum* 36:1103–1110). Thus, the present invention contemplates the use of the subject compounds in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By promoting chondrogenesis, the subject compounds can be used to particularly addresses this problem, by causing the implanted cells to become more adaptive to the new environment and effectively resemble hypertrophic chondrocytes of an earlier developmental stage of the tissue. Thus, the action of chondrogensis in the implanted tissue, as provided by the subject compounds, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) Clin Orthop Relat Red 252:129), isolated chondrocytes (Grande et al. (1989) J Orthop Res 7:208; and Takigawa et al. (1987) Bone Miner 2:449), and chondrocytes attached to natural or synthetic polymers (Walitani et al. (1989) J Bone Jt Surg 71B:74; Vacanti et al. (1991) Plast Reconstr Surg 88:753; von Schroeder et al. (1991) J Biomed Mater Res 25:329; Freed et al. (1993) J Biomed Mater Res 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment, the implants are contacted with a petidomimetic of the present invention during the culturing process in order to induce and/or maintain differentiated chondrocytes in the culture and to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In yet a further embodiment, the subject compounds can be used to prevent osteoclastic bone resorption, such as which occurs during postmenopausal osteoporosis. Such a therapy would be directed at the action of p60-src, or downstream transduction proteins, which has been shown to be required and essential for osteoclastic bone resorption (Yoneda etal. (1993) *J Clin Invest* 91:2791–2795; and Tanaka etal. (1993) *FEBS Lett* 313:85–89). In a preferred embodiment, the therapeutic preparation contains a peptidomimetic which inhibits osteoclastic bone resorption, and a second agent which stimulates new bone formation. There are several indications that integrins may mediate the differentiation of osteoblasts, analagous to the stimulation of chondroblasts, suggesting that the subject compounds can be used to induce bone formation.

The subject compounds also have utility in production of transgenic animals. In particular, the peptidomimetics of the present invention can be use to offset detrimental side effects associated with overexpression of a recombinant protein in the tissue or bodily fluid of a transgenic animal. For instance, the present inhibitors can be used to prevent detrimental consequences associated with overexpression of a growth factor, or to prevent hyperinsulinema in transgenic animals producing recombinant insulin. Use of the present inhibitors to this end can facilitate tolerance to increased levels of recombinant protein production, and thereby increase the yield per animal.

The subject peptidomimetics can also be used as speciality chemicals, such as to facilitate the dissection of intracellular signalling pathways. For example, since the discovery of insulin and its receptor, the downstream elements responsible for the pleiotropic insulin signal have been difficult to define. Utilizing the present compounds, particular pathways originating from the insulin receptor can be inhibited in order to ascertain the role of each signal pathway in the biological repsonse of the cell to insulin.

In yet another embodiment, the subject compounds can be utilized in an insecticide formulation, such as to destroy fruit flies. For example, inhibitors of the SH2-containing proteins corkscrew or Dsrc, can be used to kill Drosphilia. The substituents on the azepine core can be chosen so as to maximize absorption by mature flies or by larva.

The invention now being generally described, it will be more readily understood by reference to the following examples which are included merely for purposes of illustration of certain aspects and embodiments of the present invention, and are not intended to limit the invention.

EXAMPLE 1

α-Hydroxy-N-benzyloxycarbonylglycine (22A)

Benzyl carbamate (63 g, 0.05 mol) was stirred with glyoxylic acid monohydrate (5.09 g, 0.055 mol) in dry ether (50 mL). The crystalline product 22A (7.81 g, 73%) formed was filtered and washed with ether.

EXAMPLE 2

α-(Isopropylthio)-N-(benzyloxycarbonyl)glycine (22B)

α-hydroxy-N-benzyloxycarbonylglycine 22A (5.57 g, 0.027 mol) of Example 1 was stirred with isopropylmercaptan (8.29 g, 0.11 mol) in glacial acetic acid (26.5 mL) at 0° C. Conc $H_2SO_4$ (0.27 mL) was added and the mixture stirred for 2 days at room temperature. The mixture was then poured into ice and the organic layer extracted with ethyl acetate. The ethyl acetate solution was washed with water, 5% $NaHCO_3$, dried over $MgSO_4$, solvent removed to give 22B in 94% yield. This was used without further purification.

EXAMPLE 3

2-[N-(α-(Isopropylthio)-N-(benzyloxycarbonyl)-glycinyl)amino]benzophenone (24)

α-(isopropylthio)-N-(benyloxycarbonyl)glycine 22B was dissolved in methylene chloride (200 mL) under nitrogen atmosphere at 0° C. in a three necked flask carrying an additional funnel. To the stirred solution was added N-methylmorpholine (2.11 mL, 19.3 mmol) followed by isobutylchloroformate (2.48 mL, 19.2 mmol). This was stirred for 15 minutes at 0° C. and then heated to reflux. To the refluxing reaction mixture was added a solution of 2-aminobenzophenone 23 (3.59 g, 18.19 mmol) in dry methylene chloride (26 mL) over 20 minutes. The reaction mixture was stirred for 20 more minutes after the addition and then left stirring overnight at room temperature. The reaction mixture was washed with 10% citric acid, saturated sodium bicarbonate solution and brine, then dried over magnesium sulphate. Solvent evaporated at reduced pressure to give 9.30 g of the crude product 24. This was used without further purification.

EXAMPLE 4

2-[-(α-Amino-$N^α$-(benzylcarbonyl)glycinyl) amino]-benzophenone (25).

The crude product 24 (9.3 g, 20.17 mmol) was dissolved in 133 mL of dry tetrahydrafuran. This solution was saturated with ammonia at 0° C. for 30 minutes and then mercuric chloride (6 g, 22.09 mmol) was added in one portion to the stirred solution while ammonia gas was bubbled through the solution. After bubbling ammonia gas for 2 hours at 0° C. it was bubbled for an additional hour at room temperature. The suspended solids were filtered and the solvent evaporated to yield 25 (9.7 g) which was used without further purification.

EXAMPLE 5

1,3-Dihydro-5-phenyl-3(R,S)-[(benzyloxycarbonyl)-amino]-2H-1,4-benzodiazepin-2-one (26).

Crude α-amino-glycinamide 25 (9.7 g, 24.04 mmol) was dissolved in 182 mL of glacial acetic acid, and ammonium acetate (8.73 g, 113.37 mmol) was added to this solution under nitrogen atmosphere, with the resulting reaction mixture stirred overnight under dry conditions. This mixture was concentrated under reduced pressure and stirred with 105 mL ethyl acetate and 25 mL 1N sodium hydroxide solution for 30 minutes. The solid formed was filtered and washed with ethyl acetate to give the pure diazepine 26. The ethyl acetate washings was further concentrated to give an additional amount of product and washings further purified on flash column chromatography on silica gel (40% ethyl acetate, 60% hexane). The final yield of pure product was 5.89 g (75.2% yield from 2-aminobenzophenone).

EXAMPLE 6

1,3Dihydro-5-phenyl-1-(ethoxy carbonyl methyl)-(R,S)-[(benzyloxycarbonyl)-amino]2H-1,4-benzodiazepin-2-one (27).

Sodium hydride (60% suspension in mineral oil) (0.53 g, 13.5 mmol) was stirred with dry dimethyl formamide (3 mL) under argon atmosphere in an ice bath. To this was added the benzodiazepine 26 of Example 5 (5 g, 12.98 mmol) in DMF (12 mL) and the mixture was stirred for 40 minutes at 0° C. Ethyl bromoacetate (1.47 mL, 2.22 g, 13.3 mmol) was added to this and the mixture stirred further for an hour at 0° C., then overnight at room temperature. The solvent was removed in vacuo and the residue treated with ice and extracted with dichloromethane (150×3 mL). The dichloromethane extracts were washed with water, brine and dried over magnesium sulphate to give 6 g of the 1-substituted diazepine 27. This was saponified without further purification.

EXAMPLE 7

1(Carboxymethyl)-1,3-Dihydro-5-phenyl-3(R,S)-[(benzyloxycarbonyl)-amino]2H-1,4-benzodiazepin-2-one (29)

Crude product 27 of Example 6 (6 g, 12.73 mmol) was dissolved in dioxane (15 mL) and water (15 mL) and cooled in an ice bath. 2N sodium hydroxide was added to this solution till pH of the solution reached 10. The heterogenous mixture was stirred at room temperature until it became homogenous. The homogenous layer was extracted with ether, and the aqueous layer acidified to pH 2 using 4N HCl. This was extracted with dichloromethane (150×3 mL), and dried over magnesium sulphate to give 5.52 g of 29 (95% yield from compound 26) as a pure white solid.

EXAMPLE 8

1,3-Dihydro-5-phenyl-1-[(methoxy isoleucyl)-carboxy methyl[-5-phenyl-3-R,S-[(benzoxycarbonyl)-amino]2H-1,4-benzodiazepin-2-one (30)

To the benzodiazepin-2-one 29 (0.55 g, 1.23 mmol), in tetrahydrofuran (4 mL) at −20° C. under argon, was added NMM (0.14 mL, 1.23 mmol) followed by isobutylchloroformate (9.16 mL, 1.23 mmol). The mixture was stirred for 5 minutes, and then 0.14 mL (1.23 mmol) of NMM was added, followed by isoleucine methyl ester (0.22 g, 1.23 mmol) in tetrahydrafuran. This solution was stirred for 1 hour at −20° C., then 2 hours at room temperature. Tetrahydrafuran was removed in vacuum and the resulting solid was dissolved in ethylacetate, and the salts filtered off. The ethyl acetate extract was washed with 5% citric acid, 5% sodium bicarbonate solution, water, brine and dried over $MgSO_4$. Solvent evaporated to give 0.70 g of the crude 2-isoleucyl diazepine 30. This was chromatographed on silica gel column using 40% ethyl acetate/60% hexane to give 0.59 g of pure 30 (92% yield).

EXAMPLE 9

3(R,S)-Amino-1,3-dihydro-1-[(methoxy isoleucyl) carboxymethyl]-5-phenyl-2H-1,4-benzodiazepin-2-one (31)

Compound 30 (0.59 g, 1.02 mmol) was dissolved in 15 mL of methanol under argon atmosphere. 10% Pd/C (0.05 g) was added and then the system was evacuated, and twice flushed with argon and twice with hydrogen before hydrogenation was started. The mixture was allowed to stir overnight with hydrogen from a balloon. It was then cautiously filtered using a sintered glass funnel carrying filter agent. The residue was washed with warm methanol twice and the filtrate was evaporated in vacuum to give the deprotected compound 31 (0.41 g, 91% yield).

EXAMPLE 10

1,3-Dihydro-1-[(methoxy isoleucyl)carbonylmethyl]-5-phenyl-3(R,S)-{[(N-fluorenylmethoxy carbonyl)-phosphonotyrosyl]dimethyl ester-amino}-2H-1,4-benzodiazepin-2-one (32).

N-Fmoc phosphotyrosine dimethyl ester (0.14 g, 0.28 mmol) was stirred with THF under argon at −20° C. To this was added NMM (0.03 mL, 0.28 mmol) and isobutylchloroformate (0.04 mL, 0.28 mmol) and stirred for 5 minutes. To this was further added NMM (0.03 mL, 0.28 mmol) and compound 31 (0.12 g, 0.28 mmol) in 3 mL of DMF and stirred for 1 h at −20° C. and 2 h at room temperature. Solvent evaporated under vacuum and the remaining solid was dissolved in ethyl acetate and filtered. Ethyl acetate extracts were washed with 5% citric acid, 5% $NaHCO_3$, water, brine and dried over $MgSO_4$. Solvent evaporated to give crude 32 (0.25 g) which was purified on column chromatography using. 5% ethanol in ethyl acetate.

EXAMPLE 11

1,3-Dihydro-1-[(methoxy-L-isoleucyl) carbonylmethyl)-5-phenyl-3(R,S)-{[(N-fluorenylmethoxy carbonyl)phosphono-L-tyrosyl]amino}-2H-1,4-benzodiazepin-2-one To a solution of isobutylene in 3 mL of dichloromethane (prepared by bubbling isobutylene for 10 minutes) was added bromo trimethyl silane (0.038 mL, 0.29mmol). After 5 minutes compound 32 (0.05 g, 0.05 mmol) in 1 mL of dichloromethane was added, and the mixture left stirring overnight at room temperature. The dichloromethane was evaporated from the reaction mixture, which was then evaporated twice from chloroform and from 2 mL of methanol to give solid 33 (0.03 g, 62.5%) which was dried under vacuum. This was further purified using analytical C18 HPLC using acetonitrile\water as solvent system.

EXAMPLE 12

1,3-Dihydro-1-[(methoxy-L-isoleucyl) carbonylmethyl)-5-phenyl-3(R,S)-[(phosphono-L-tyrosyl)dimethyl ester amino]-2H-1,4-benzodiazepin-2-one (34)

Compound 32 (0.13 g, 0.14 mmol) was dissolved in DMF and 0.046 mL (0.46 mmol) of piperdine was added and the mixture was stirred for 0.5 hours. The the solvent was removed and the remaining solid was washed with hexane and dried in vacuum to give 0.095 g (97%) of 34.

EXAMPLE 13

1,3-Dihydro-1-[(methoxy-L-isoleucyl) carbonylmethyl-5-phenyl-3(R,S)-{[(N-acetyl)-phosphono-tyrosyl)dimethyl ester amino]-2H-1,4-benzodiazepin-2-one (35)

To the compound 34 (0.10 mg, 0.14 mmol), in dry THF at −20° C., was added NMM (0.016 mL, 0.14 mmol), followed by acetyl chloride (0.011 mL, 0.14 mmol) in THF. This was stirred at −20° C. for 1 h and room temperature overnight. Solvent was removed under vacuum and the remaining solid dissolved in ethyl acetate and washed with water and dried over magnesium sulphate. Solvent was evaporated and crude 35 (0.09 g, 85%) was purified using HPLC, 0.5% ethanol/ethyl acetate.

EXAMPLE 14

1,3Dihydro-1-[(methoxy-L-isoleucyl)-carbonylmethyl)-5-phenyl-3(R,S)-{[(N-acetyl)-phosphono-L-tyrosyl]amino}-2H-1,4-benzodiazepin-2-one (36)

To isobutylene in dichloromethane (3 mL) was added bromotrimethyl silane ("TMSB", 0.027 mL, 0.24 mmol) and stirred for 5 minutes. To this was added compound 35 (0.033 g, 0.04 mmol) in 1 mL of dichlormethane and stirred overnight at room temperature. Solvent was removed, and evaporated twice with chloroform and then any methanol was removed to give 36 (0.022 g , 69%). This was purified on analytical HPLC C18 column using water acetonitrile as solvent system and the diasteromers separated.

EXAMPLE 15

Demonstration of the effect of (36) on Middle T/fyn interaction

Figure 6:
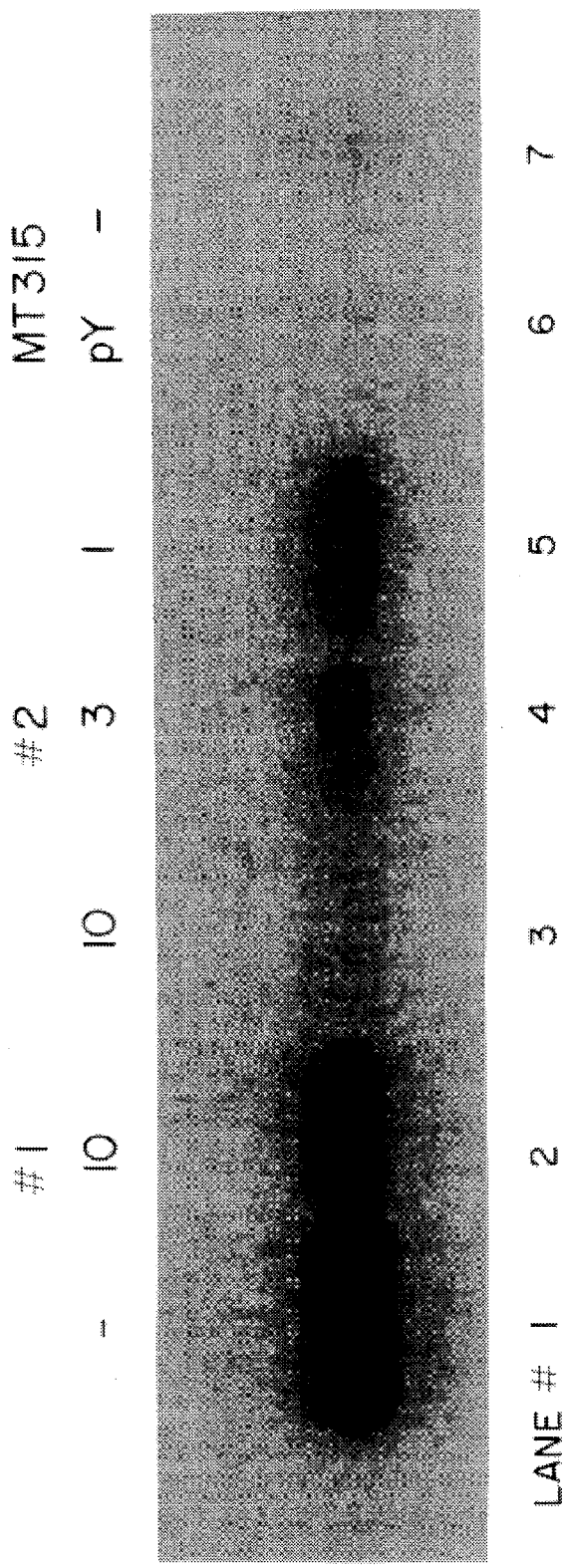
FIG. 6 is an autoradiogram of a gel visualizing the ability of a GST-fyn fusion protein to bind to phosphorylated polyoma middle T antigen, in the presence and absense of a peptidomimetic of the present invention.

Approximately 10 μg of a GST-Fyn fusion protein bound to 10 μl of glutathione-Sepharose beads were incubated with 90 μl of buffer (TEB, pH 9.0) and 10 μl of DMSO or DMSO containing an isomer (#1 or #2) of compound 36 (lanes 2 and 3 equal $3.95 \times 10^{-4}$M; lane 4 equals $1.32 \times 10^{-4}$M; lane 5 equals $3.95 \times 10^{-5}$M). Lane 1 contains no inhibitor. The lanes labeled "MT 315" (lanes 6 and 7) are reaction mixtures as above, but having 20 μg of peptide (middle T residues EEYMPMED) instead of the benzodiazepine 36. The label "pY" indicates the peptide was phosphorylated, while unphosphorylated peptide is designated as "–". The reaction mixtures were incubated for 1 hour, then 100 μL $^{32}$P-labeled Middle T (polyoma), prepared from baculovirus co-expression of middle T and src in Sf9 cells, were added to each reaction and incubated for 1 hour more at 4° C. The sepharose was washed with twice with PBS, and once with distilled water, boiled in SDS dissociation buffer, and run on a 7.5% acrylamide SDS gel. Labeled MT was visualized on the gel by autoradiography, and the inhibition of MT/fyn interaction determined. While both isomers of 36 displayed inhibitory action, FIG. 6 illustrates that isomer #2 is a more potent inhibitor of the SH2 mediated interaction of middle T and fyn.

EXAMPLE 16

Demonstration of the effect of (36) and (33) on SH2 interactions

In order to assess the inhibitory activity of the present peptidomimetics, the ability of the subject compounds to inhibit the interaction between a specific peptide and an SH2 domain was determined. Various SH2 domains were subcloned in frame with the glutathione-S-transferase affinity tag of the pGEX vector system (Pharmacia catalog no. PGEX-4T-3). The resulting pGEX-E2 construct encoded a glutathione-S-transferase (GST)/SH2 fusion protein (Smith et al. (1988) *Gene* 67:31–40). The pGEX construct was introduced into *E. coli* by transfromation, and the transformants grown in liquid media (LB) in the presence of IPTG. Purification of GST/E2 fusion protein was by standard protocols (*Current Protocols in Molecular Biology*, eds. Ausubel et al. (NY:John Wiley & Sons, 1991 ); Pharmacia instruction booklet (for catalog no. 27–4570)) using a glutathione-sepharose column (Pharmacia catalog no. 27–4570). Briefly, the cells were pelleted and resuspended in buffer A (50 mM TRIS (pH7.5), 2 mM EDTA, 250 mM NaCl, 5% glycerol (V/V), 1% Tween (V/V), 1% Triton X 100 (V/V)), to which 2 mM PMSF and 15 mM 2-mercaptoethanol were added. Bacteria were mechanically disrupted by sonication or by microfluidizer, and the soluble fraction of the lysate was absorbed with glutathione-agarose beads which had been rehydrated in buffer A. Absorption was for 30 minutes to 14 hours at 4° C. during which the beads were maintained in suspension by rocking. Subsequently, the beads were washed 3 times in cold buffer A followed by 5 washes in 50 mM Tris, pH 8.0

The peptide against which the subject compounds were tested was of the sequence EPQYEEIPIYL. In one instance, in order to detect the peptide it was labeled using conjugated with FITC. The protocol for the conjugation of proteins with amine reactive probes (Molecular Probes) was followed. Briefly, 10 mgs of FITC in 100 μL of DMSO was added dropwise to 10 mgs of peptide. The material was incubated for 1 hr at room temperature with shaking. 100 μL of fresh 1.5M hydroxylamine pH 8.0, was added to the reaction mix and the incubation continued for 30 minutes. The incorporated label was separated from unincorporated by chromatography in a c18 column with typical TFAlacetonitrile buffers, using conditions described above. Peptide containing peaks were identified by their ability to specifically bind to the appropriate SH2 domain. For subsequent studies, the peptide was labeled before cleavage from the support resin used for its synthesis.

Figure 2D:
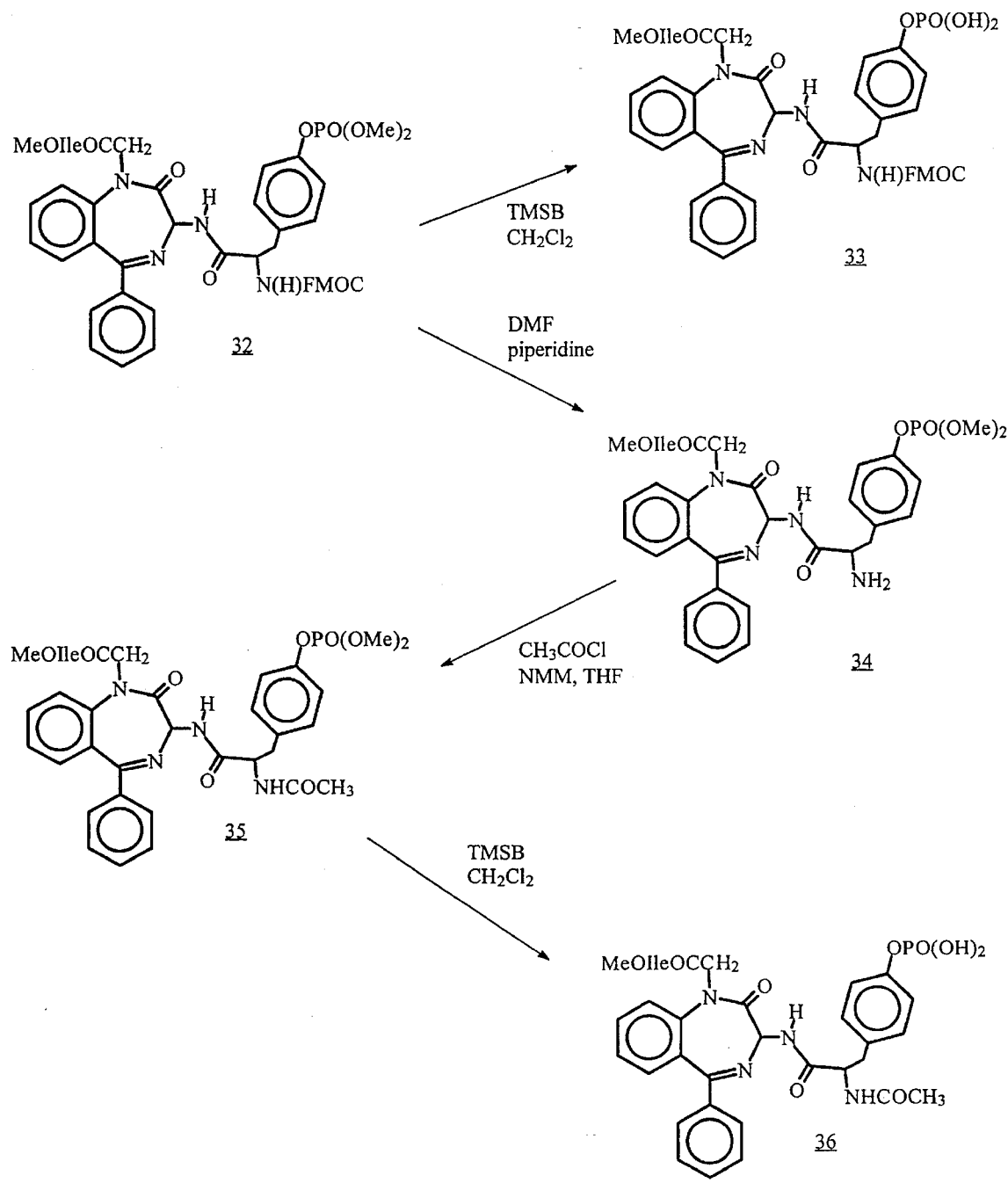

The IDEXX lck-SH2 binding assay was carried out employing the GST-SH2 fusion protein, the FITC-labeled peptide, and a sample peptidomimetic of the present invention which was N-protected with either an FMOC moiety (33 of FIG. 2D) or acetyl moiety (36 of FIG. 2D). Briefly, the SH2-beads were wash 3 times with cold (4° C.) Tris Buffered Saline (TBS), and centrifuged (5 min., 2000 g, 4° C.) between washes. The bead pellet was resuspended in TBS, diluting the beads 1/20 (v/v). The beads are subsequently kept cold before use.

The lyophilized FITC-peptide was resuspended in TBS into the volume before lyophilization (1 ml/tube), and then diluted 1/20 into TBS. The FITC-peptide was subsequently kept cold and protected from light.

Figure 7:
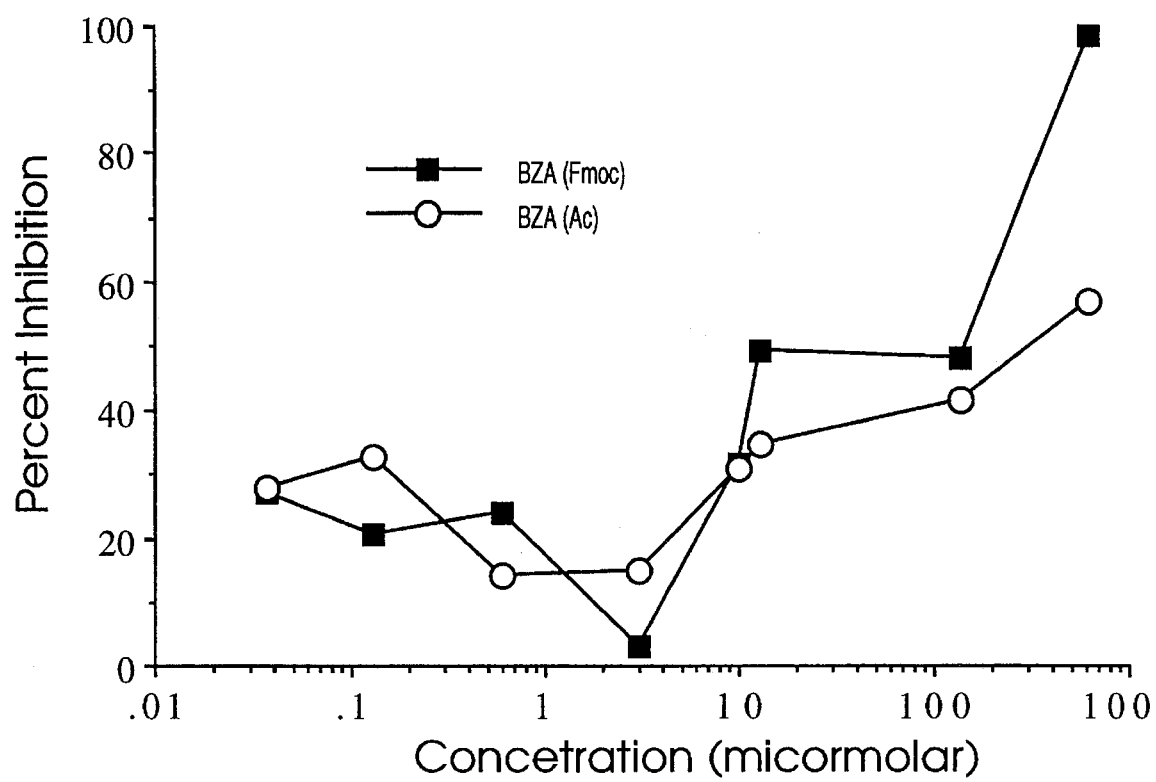
FIG. 7 is an inhibition profile illustrating the ability of the subject peptidomimetic to inhibit an lck-SH2 interaction.

Into the wells of an IDEXX microtiter plate (IDEXX Laboratories, Inc., Cat. No. 22–400-1, Fluoricon -CA Assay Plates) was added (i) 10 μL/well diluted SH2-beads; (ii) 10 μL/well diluted FITC-peptide solution; (iii) 20 μL/well of a solution containing the subject inhibitor or a control solution (with triplicate wells for each). The 100% SH2-peptide binding control (e.g. no inhibition) was 20 μL TBS. The zero SH2-peptide binding control (e.g. 100% inhibition) was 20 μL of a 200 mM solution of phenyl phosphate. The peptidomimetic was added in varying concentrations to yield the final concentrations as indicated in FIG. 7. The contents of each well were pipeted up and down with a multi-channel pipetter to mix, and then incubated 5–60 mins at room temperature and protected from the light.

The assay plates were then placed in the Idexx instrument and a vacuum at 25 inches Hg was applied until all of the liquid was removed from the wells. The vacuum was then shut-off and the plates washed with TBS. The vacuum was applied again to aspirate the TBS wash, and which was repeated once. The plates were then analyzed for FITC-labeled peptide binding, and the percent inhibition determined by the ability of the subject peptidomimetic to inhibit binding of the FITC-labeled peptide. The inhibition data was plotted, as shown in FIG. 7. As indicated by FIG. 7, the FMOC-derivative exhibited an $IC_{50}$ in the present system of 48.2 μM, and the Ac-derivative had an $IC_{50}$ of 270.9 μM.

All of the above-cited references and publications are hereby incorporated by reference.

Equivalents

Those skilled in the art will recognize, or be able to ascertain using no more than routine experimentation, numerous equivalents to the peptidomimetics and methods of use thereof described herein. Such equivalents are considered to be within the scope of this invention and are covered by the following claims.

I claim:
1. A compound represented by a general formula:

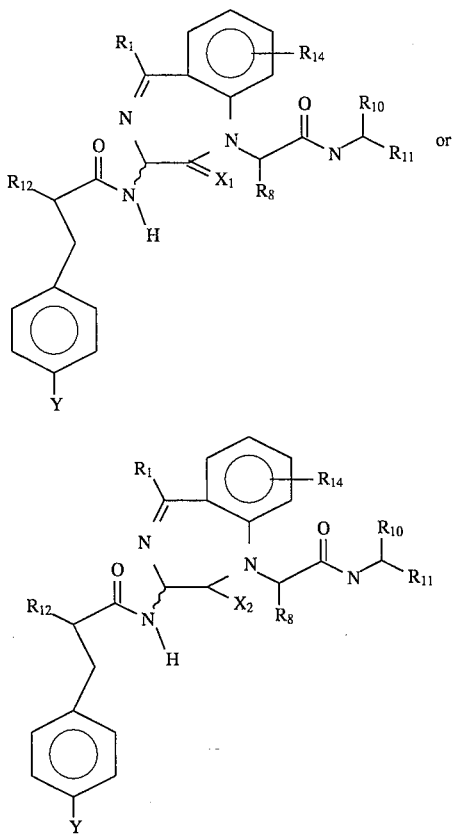

or

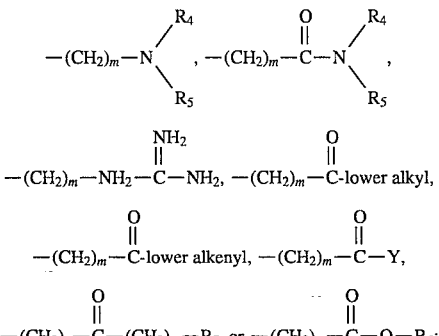

wherein $R_1$ represents hydrogen, a halogen, a lower alkyl, a lower alkenyl, a lower alkynyl, a carboxyl, an azido, $-(CH_2)_m-R_7$, $-(CH_2)_m-OH$, $-(CH_2)_m-O$-lower alkyl, $-(CH_2)_m-O$-lower alkenyl, $-(CH_2)_n-O-(CH_2)_m-R_7$, $-(CH_2)_m-SH$, $-(CH_2)_m-S$-lower alkyl, $-(CH_2)_m-S$-lower alkenyl, $-(CH_2)_n-S-(CH_2)_m-R_7$,

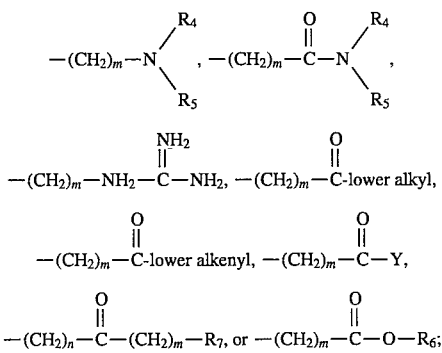

$R_4$ and $R_5$ each independently represent hydrogen, lower alkyl, lower alkenyl, $-(CH_2)_m-R_7$, $-C(O)$-lower alkyl, $-C(O)$-lower alkenyl, $-C(O)-(CH_2)_m-R_7$, or $R_4$ and $R_5$ taken together with the N atom to which they are attached complete a heterocyclic ring having from 4 to 8 atoms in the ring structure;

$R_6$ represents hydrogen, a lower alkyl, an lower alkenyl, $-(CH_2)_m-R_7$, or a pharmaceutically acceptable salt forming ion;

$R_7$ represents an aryl, a cycloalkyl, a cycloakenyl, or a heterocycle;

$R_8$ represents hydrogen, a halogen, a lower alkyl, a lower alkenyl, a lower alkynyl, a carboxyl, an azido, $-(CH_2)_m-R_7$, $-(CH_2)_m-OH$, $-(CH_2)_m-O$-lower alkyl, $-(CH_2)_m-O$-lower alkenyl, $-(CH_2)_n-O-(CH_2)_m-R_7$, $-(CH_2)_m-SH$, $-(CH_2)_m-S$-lower alkyl, $-(CH_2)_m-S$-lower alkenyl, $-(CH_2)_n-S-(CH_2)_m-R_7$, $$-(CH_2)_m-N\begin{matrix}R_4\\R_5\end{matrix},\ -(CH_2)_m-\overset{O}{\underset{\|}{C}}-N\begin{matrix}R_4\\R_5\end{matrix},$$

$$-(CH_2)_m-NH_2-\overset{NH_2}{\underset{\|}{C}}-NH_2,\ -(CH_2)_m-\overset{O}{\underset{\|}{C}}\text{-lower alkyl,}$$

$$-(CH_2)_m-\overset{O}{\underset{\|}{C}}\text{-lower alkenyl,}\ -(CH_2)_m-\overset{O}{\underset{\|}{C}}-Y,$$

$$-(CH_2)_n-\overset{O}{\underset{\|}{C}}-(CH_2)_m-R_7,\text{ or }-(CH_2)_m-\overset{O}{\underset{\|}{C}}-O-R_6;$$

$R_{10}$ represents an alpha-carbon sidechain of an amino acid residue;

$R_{11}$ represents COOH or a pharmaceutically acceptable salt thereof or a carboxy-terminal blocking group;

$R_{12}$ represents NH—$R_{17}$ or a pharmaceutically acceptable salt thereof, or an amino-terminal blocking group;

$R_{14}$ represents a halogen, a lower alkyl, a lower alkoxy, a lower alkylthio, $-NO_2$, $CF_3$, $-CN$, and $-OH$;

$R_{17}$ represents hydrogen or a C-terminally linked amino acid residue or peptide;

Y represents a phosphate or phosphate analog;

$X_1$ represents O or S; $X_2$ represents hydrogen, a lower alkyl, $-(CH_2)_m-OH$, $-(CH_2)_m-O$-lower alkyl, a carboxyl, an amine, an amide, a nitrosyl, a sulfhydryl, a sulfonyl, or a sulfonamide;

n is zero or an integer in the range of 1 to 6; m is zero or an integer in the range of 1 to 6; and p is an integer in the range of 1 to 6.

2. The compound of claim 1, wherein $R_1$ is selected from a group consisting of $-(CH_2)_m$-benzyl, $-(CH_2)_n-S-(CH_2)_m$-benzyl, $-(CH_2)_n-O-(CH_2)_m$-benzyl, $-(CH_2)_m$-pyridyl, $-(CH_2)_n-S-(CH_2)_m$-pyridyl, and $-(CH_2)_n-O-(CH_2)_m$-pyridyl, wherein each of said benzyl and pyridyl moieties can be substituted at one or more positions with a halogen, a lower alkyl, a lower alkoxy, a lower alkylthio, $-NO_2$, $-CF_3$, $-CN$, and $-OH$.

3. The compound of claim 1, wherein $R_{10}$ is an alpha-carbon sidechain of an amino acid residue selected from a group consisting of leucine, isoleucine, methionine, proline, valine, aspartic acid, and asparagine.

4. The compound of claim 1, wherein Y is selected from a group consisting of

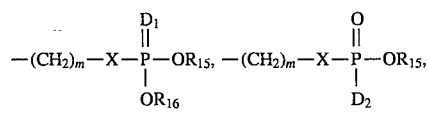

$$-(CH_2)_m-B\begin{matrix}OR_{15}\\OR_{16}\end{matrix}, \quad -(CH_2)_m-\overset{\overset{O}{\|}}{\underset{OR_{16}}{V}}-OR_{15},$$

$$-(CH_2)_m-\overset{\overset{O}{\|}}{\underset{OR_{16}}{As}}-OR_{15}, \quad -(CH_2)_m-BeF_3, \text{ and } -(CH_2)_m-AlF_3$$

wherein m is zero or an integer in the range of 1 to 6; X is absent or represents O, S, or N; $D_1$ represents O or S; $D_2$ represents $N_3$, $SH_2$, $NH_2$, or $NO_2$; and $R_{15}$ and $R_{16}$ each independent represent hydrogen, a lower alkyl, or a pharmaceutically acceptable salt, or $R_{15}$ and $R_{16}$ taken together with the O—P—O, O—B—O, O—V—O or O—As—O atoms to which they are attached complete a heterocyclic ring having from 5 to 8 atoms in the ring structure.

5. A compound represented by a general formula:

[Chemical structure diagram showing a benzodiazepine derivative with substituents $R_8$, $R_{10}$, $R_{11}$, $R_{12}$ and Y]

$R_8$ represents hydrogen or an amino acid sidechain;

$R_{10}$ represents an alpha-carbon sidechain of an amino acid residue;

$R_{11}$ represents COOH or a pharmaceutically acceptable salt thereof, or a carboxy-terminal blocking group;

$R_{12}$ represents $NH_2$ or a pharmaceutically acceptable salt thereof, or an amino-terminal blocking group; and Y represents a phosphate or phosphate analog.

6. The compound of claim 5, wherein Y is selected from a group consisting of $$-(CH_2)_m-X-\overset{\overset{D_1}{\|}}{\underset{OR_{16}}{P}}-OR_{15}, \quad -(CH_2)_m-X-\overset{\overset{O}{\|}}{\underset{D_2}{P}}-OR_{15},$$

$$-(CH_2)_m-B\begin{matrix}OR_{15}\\OR_{16}\end{matrix}, \quad -(CH_2)_m-\overset{\overset{O}{\|}}{\underset{OR_{16}}{V}}-OR_{15},$$

$$-(CH_2)_m-\overset{\overset{O}{\|}}{\underset{OR_{16}}{As}}-OR_{15},$$

$-(CH_2)_m-BeF_3$, and $-(CH_2)_m-AlF_3$ wherein m is zero or an integer in the range of 1 to 6; X is absent or represents O, S, or N; $D_1$ represents O or S; $D_2$ represents $N_3$, $SH_2$, $NH_2$, or $NO_2$; and $R_{15}$ and $R_{16}$ each independently represent hydrogen, a lower alkyl, or a pharmaceutically acceptable salt, or $R_{15}$ and $R_{16}$ taken together with the O—P—O, O—B—O, O—V—O or O—As—O atoms to which they are attached complete a heterocyclic ring having from 5 to 8 atoms in the ring structure.

7. The compound of claim 5, wherein $R_{10}$ is an alpha-carbon sidechain of an amino acid residue selected from a group consisting of leucine, isoleucine, methionine, proline, valine, aspartic acid, and asparagine.

8. The compound of claim 5, selected from a group consisting of 1,3-Dihydro-1-[(L-isoleucyl)-carbonylmethyl)-5-phenyl-3(R,S)-{[(N-acetyl)-phosphono-L-tyrosyl]amino}-2H-1,4-benzodiazepin-2-one; 1,3-Dihydro-1-[(L-methionyl)-carbonylmethyl)-5-phenyl-3(R,S)-{[(N-acetyl)-phosphono-L-tyrosyl]amino}-2H-1,4-benzodiazepin-2-one; 1,3-Dihydro-1-[(L-leucyl)-carbonylmethyl)-5-phenyl-3(R,S)-{[(N-acetyl)-phosphono-L-tyrosyl]amino}-2H-1,4-benzodiazepin-2-one; 1,3-Dihydro-1-[(L-prolyl)-carbonylmethyl)-5-phenyl-3(R,S)-{[(N-acetyl)-phosphono-L-tyrosyl]amino}-2H-1,4-benzodiazepin-2-one; 1,3-Dihydro-1-[(L-valyl)-carbonylmethyl)-5-phenyl-3(R,S)-{[(N-acetyl)-phosphono-L-tyrosyl]amino}-2H-1,4-benzodiazepin-2-one; 1,3-Dihydro-1-[(L-aspartyl)-carbonylmethyl)-5-phenyl-3(R,S)-{[(N-acetyl)-phosphono-L-tyrosyl]amino}-2H-1,4-benzodiazepin-2-one; 1,3-Dihydro-1-[(L-asparginyl)-carbonylmethyl)-5-phenyl-3(R,S)-{[(N-acetyl)-phosphono-L-tyrosyl]amino}-2H-1,4-benzodiazepin-2-one; 1,3-Dihydro-1-[(L-isoleucyl)-carbonylmethyl)-5-phenyl-3(R,S)-{[(N-acetyl)-4-boronylphenylalanine]amino}-2H-1,4-benzodiazepin-2-one; 1,3-Dihydro-1-[(L-methionyl)-carbonylmethyl)-5-phenyl-3(R,S)-{[(N-acetyl)-4-boronylphenylalanine]amino}-2H-1,4-benzodiazepin-2-one; 1,3-Dihydro-1-[(L-leucyl)-carbonylmethyl)-5-phenyl-3(R,S)-{[(N-acetyl)-4-boronylphenylalanine]amino}-2H-1,4-benzodiazepin-2-one; 1,3-Dihydro-1-[(L-prolyl)-carbonylmethyl)-5-phenyl-3(R,S)-{[(N-acetyl)-4-boronylphenylalanine]amino}-2H-1,4-benzodiazepin-2-one; 1,3-Dihydro-1-[(L-valyl)-carbonylmethyl)-5-phenyl-3(R,S)-{[(N-acetyl)-4-boronylphenylalanine]amino}-2H-1,4-benzodiazepin-2-one; 1,3-Dihydro-1-[(L-aspartyl)-carbonylmethyl)-5-phenyl-3(R,S)-{[(N-acetyl)-4-boronylphenylalanine]amino}-2H-1,4-benzodiazepin-2-one; 1,3-Dihydro-1-[(L-asparginyl)-carbonylmethyl)-5-phenyl-3(R,S)-{[(N-acetyl)-4-boronylphenylalanine]amino}-2H-1,4-benzodiazepin-2-one; 1,3-Dihydro-1-[(L-isoleucyl)-carbonylmethyl)-5-phenyl-3(R,S)-{[(N-acetyl)-4-arsenylphenylalanine]amino}-2H-1,4-benzodiazepin-2-one; 1,3-Dihydro-1-[(L-methionyl)-carbonylmethyl)-5-phenyl-3(R,S)-{[(N-acetyl)-4-arsenylphenylalanine]amino}-2H-1,4-benzodiazepin-2-one; 1,3-Dihydro-1-[(L-leucyl)-carbonylmethyl)-5-phenyl-3(R,S)-{[(N-acetyl)-4-arsenylphenylalanine]amino}-2H-1,4-benzodiazepin-2-one; 1,3-Dihydro-1-[(L-prolyl)-carbonylmethyl)-5-phenyl-3(R,S)-{[(N-acetyl)-4-arsenylphenylalanine]amino}-2H-1,4-benzodiazepin-2-one; 1,3-Dihydro-1-[(L-valyl)-carbonylmethyl)-5-phenyl-3(R,S)-{[(N-acetyl)-4-arsenylphenylalanine]amino}-2H-1,4-benzodiazepin-2-one; 1,3-Dihydro-1-[(L-aspartyl)-carbonylmethyl)-5-phenyl-3(R,S)-{[(N-acetyl)-4-arsenylphenylalanine]amino}-2H-1,4-benzodiazepin-2-one; 1,3-Dihydro-1-[(L-asparginyl)-carbonylmethyl)-5-phenyl-3(R,S)-{[(N-acetyl)-4-arsenylphenylalanine]amino}-2H-1,4-benzodiazepin-2-one; 1,3-Dihydro-1-[(L-isoleucyl)-carbonylmethyl)-5-phenyl-3(R,S)-{[(N-acetyl)-4-phosphonomethylphenylalanine]

amino}-2H-1,4-benzodiazepin-2-one; 1,3-Dihydro-1-[(L-methionyl)-carbonylmethyl)-5-phenyl-3(R,S)-{[(N-acetyl)-4-phosphonomethylphenylalanine]amino}-2H-1,4-benzodiazepin-2-one; 1,3-Dihydro-1-[(L-leucyl)-carbonylmethyl)-5-phenyl-3(R,S)-{[(N-acetyl)-4-phosphonomethylphenylalanine]amino}-2H-1,4-benzodiazepin-2-one; 1,3-Dihydro-1-[(L-prolyl)-carbonylmethyl)-5-phenyl-3(R,S)-{[(N-acetyl)-4-phosphonomethylphenylalanine]amino}-2H-1,4-benzodiazepin-2-one; 1,3-Dihydro-1-[(L-valyl)-carbonylmethyl)-5-phenyl-3(R,S)-{[(N-acetyl)-4-phosphonomethylphenylalanine]amino}-2H-1,4-benzodiazepin-2-one; 1,3-Dihydro-1-[(L-aspartyl)-carbonylmethyl)-5-phenyl-3(R,S)-{[(N-acetyl)-4-phosphonomethylphenylalanine]amino}-2H-1,4-benzodiazepin-2-one; 1,3-Dihydro-1-[(L-asparginyl)-carbonylmethyl)-5-phenyl-3(R,S)-{[(N-acetyl)-4-phosphonomethylphenylalanine]amino}-2H-1,4-benzodiazepin-2-one; 1,3-Dihydro-1-[(L-isoleucyl)-carbonylmethyl)-5-phenyl-3(R,S)-{[(N-acetyl)-4-vanadylphenylalanine]amino}-2H-1,4-benzodiazepin-2-one; 1,3-Dihydro-1-[(L-methionyl)-carbonylmethyl)-5-phenyl-3(R,S)-{[(N-acetyl)-4-vanadylphenylalanine]amino}-2H-1,4-benzodiazepin-2-one; 1,3-Dihydro-1-[(L-leucyl)-carbonylmethyl)-5-phenyl-3(R,S)-{[(N-acetyl)-4-vanadylphenylalanine]amino}-2H-1,4-benzodiazepin-2-one; 1,3-Dihydro-1-[(L-prolyl)-carbonylmethyl)-5-phenyl-3(R,S)-{[(N-acetyl)-4-vanadylphenylalanine]amino}-2H-1,4-benzodiazepin-2-one; 1,3-Dihydro-1-[(L-valyl)-carbonylmethyl)-5-phenyl-3(R,S)-{[(N-acetyl)-4-vanadylphenylalanine]amino}-2H-1,4-benzodiazepin-2-one; 1,3-Dihydro-1-[(L-aspartyl)-carbonylmethyl)-5-phenyl-3(R,S)-{[(N-acetyl)-4-vanadylphenylalanine]amino}-2H-1,4-benzodiazepin-2-one; 1,3-Dihydro-1-[(L-asparginyl)-carbonylethyl)-5-phenyl-3(R,S)-{[(N-acetyl)-4-vanadylphenylalanine]amino}-2H-1,4-benzodiazepin-2-one.

* * * * *